(12) United States Patent
Okamoto et al.

(10) Patent No.: US 8,394,082 B2
(45) Date of Patent: Mar. 12, 2013

(54) MEDICAL SYSTEM

(75) Inventors: Yasuhiro Okamoto, Hachioji (JP);
Kazuo Banju, Hachioji (JP)

(73) Assignee: Olympus Medical Systems Corp. (JP)

( * ) Notice: Subject to any disclaimer, the term of this patent is extended or adjusted under 35 U.S.C. 154(b) by 331 days.

(21) Appl. No.: 12/777,336

(22) Filed: May 11, 2010

(65) Prior Publication Data

US 2010/0318100 A1  Dec. 16, 2010

Related U.S. Application Data

(63) Continuation of application No. PCT/JP2009/067803, filed on Oct. 14, 2009.

(30) Foreign Application Priority Data

Nov. 14, 2008 (JP) ................................. 2008-292163

(51) Int. Cl.
*A61B 19/00* (2006.01)
(52) U.S. Cl. ............................................ 606/1; 606/130
(58) Field of Classification Search .............. 606/1, 130; 345/156
See application file for complete search history.

(56) References Cited

U.S. PATENT DOCUMENTS

| 6,120,433 | A | 9/2000 | Mizuno et al. | |
|---|---|---|---|---|
| 2001/0000663 | A1* | 5/2001 | Shahoian et al. | 345/156 |
| 2008/0065103 | A1* | 3/2008 | Cooper et al. | 606/130 |

FOREIGN PATENT DOCUMENTS

| EP | 1 779 801 | 5/2007 |
|---|---|---|
| EP | 2 123 211 | 11/2009 |
| JP | 7-504363 | 5/1995 |
| JP | 8-173442 | 7/1996 |
| JP | 2003-284726 | 10/2003 |
| JP | 2003-325436 | 11/2003 |
| JP | 2004-215905 | 8/2004 |
| JP | 2007-185385 | 7/2007 |
| JP | 2008-212349 | 9/2008 |
| WO | WO 2007/111571 | 10/2007 |

OTHER PUBLICATIONS

Office Action issued by the Japanese Patent Office on Jun. 29, 2010 in connection with corresponding Japanese Patent Application No. 2010-518657.
Translation of Office Action issued by the Japanese Patent Office on Jun. 29, 2010 in connection with corresponding Japanese Patent Application No. 2010-518657.
International Search Report and Written Opinion mailed Nov. 17, 2009 in corresponding PCT International Application No. PCT/JP2009/067803.
Search Report issued by European Patent Office and received by applicant on Nov. 15, 2011 in connection with corresponding EP patent application No. EP 09 825 996.

* cited by examiner (Continued)

*Primary Examiner* — Bill Thomson
*Assistant Examiner* — Jeffrey Lipitz
(74) *Attorney, Agent, or Firm* — Ostrolenk Faber LLP

(57) ABSTRACT

A medical system includes an insertion slave apparatus to be inserted into a body, a treatment slave apparatus to be inserted into the body together with the insertion slave apparatus to treat an object, an insertion master portion having a similar figure to the insertion slave apparatus and including a movable portion, wherein the insertion slave apparatus is to perform following actuation according to operation input to the insertion master portion, a treatment master portion to be operated by an operator, wherein the treatment slave apparatus is to perform following actuation according to operation input to the treatment master portion, and a connecting portion coupling the insertion master portion and the treatment master portion to each other, wherein the movable portion is to be moved through the connecting portion to operate the insertion master portion by holding and operating the treatment master portion.

3 Claims, 26 Drawing Sheets

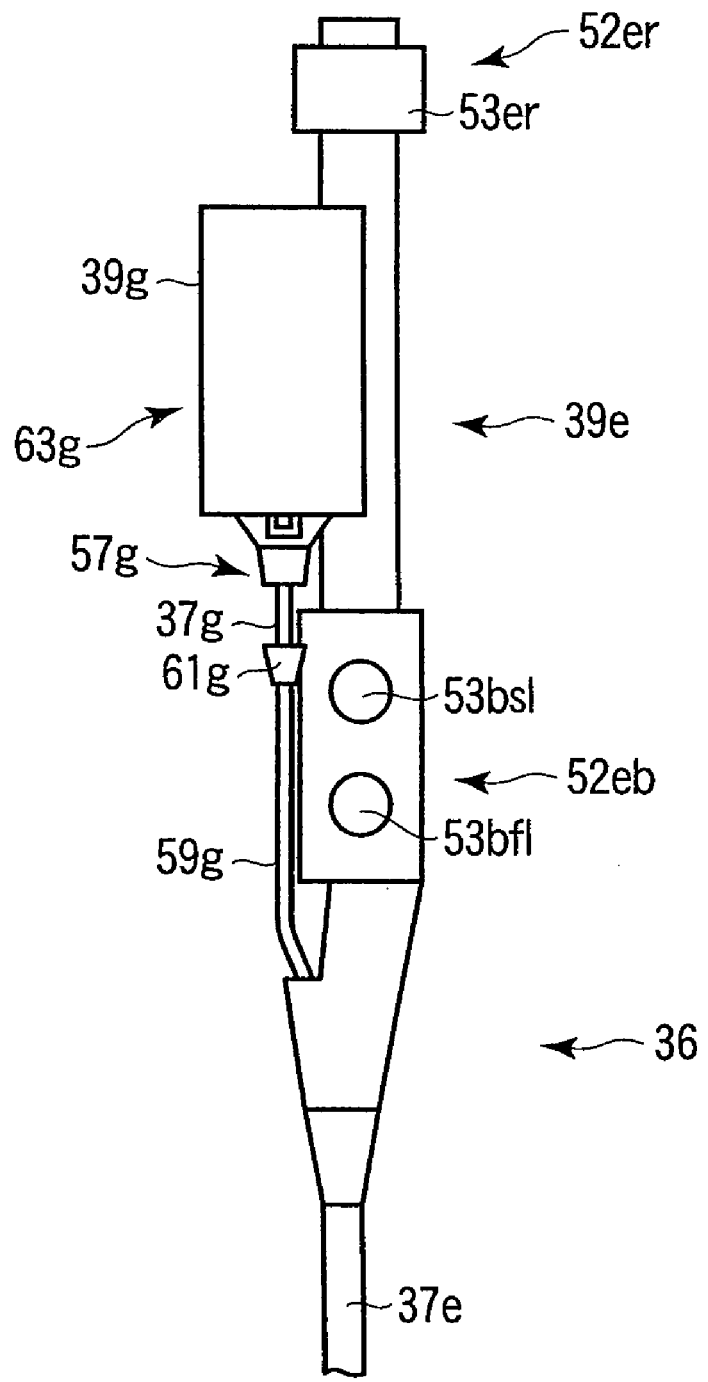
F I G. 2

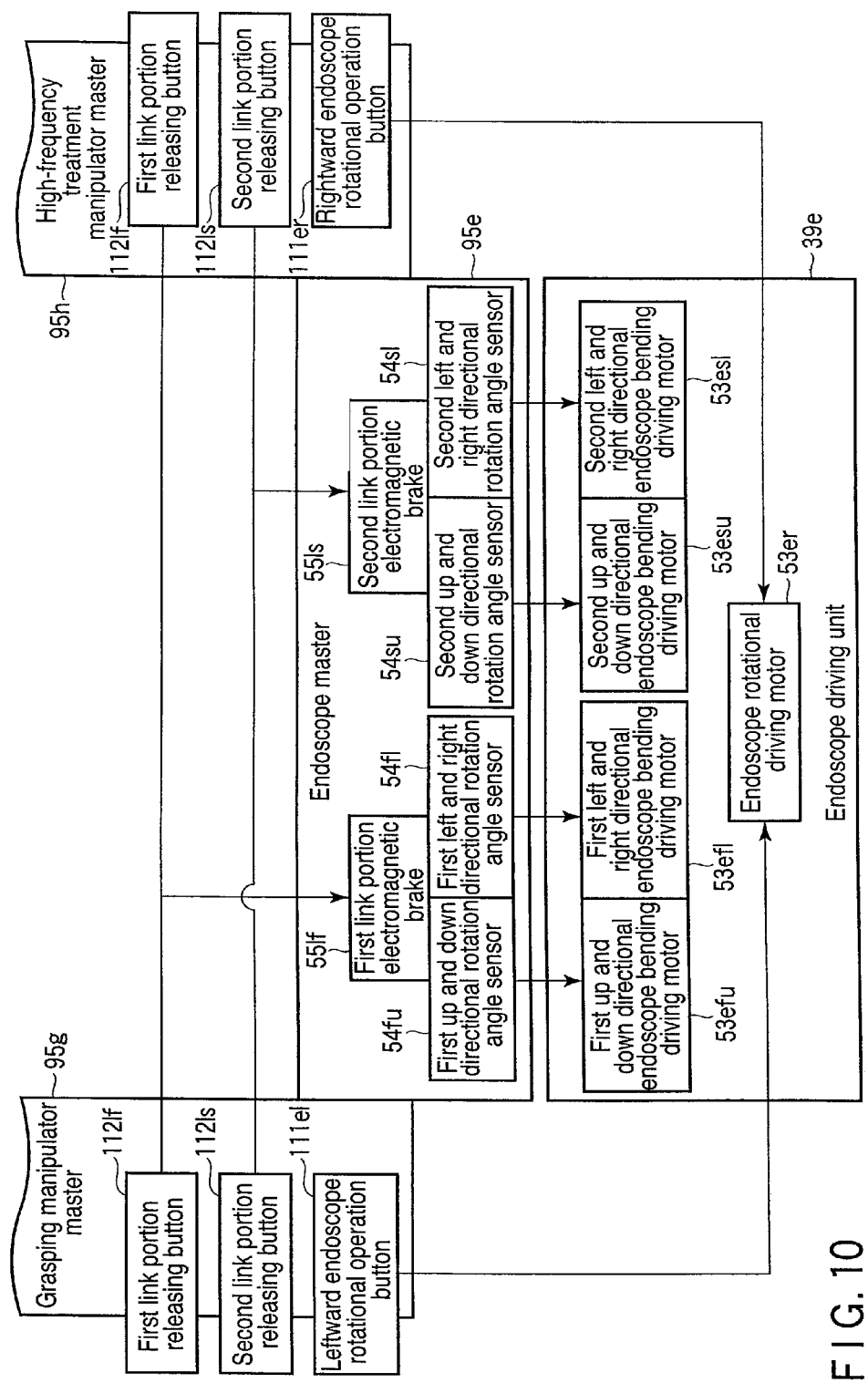
F I G. 10

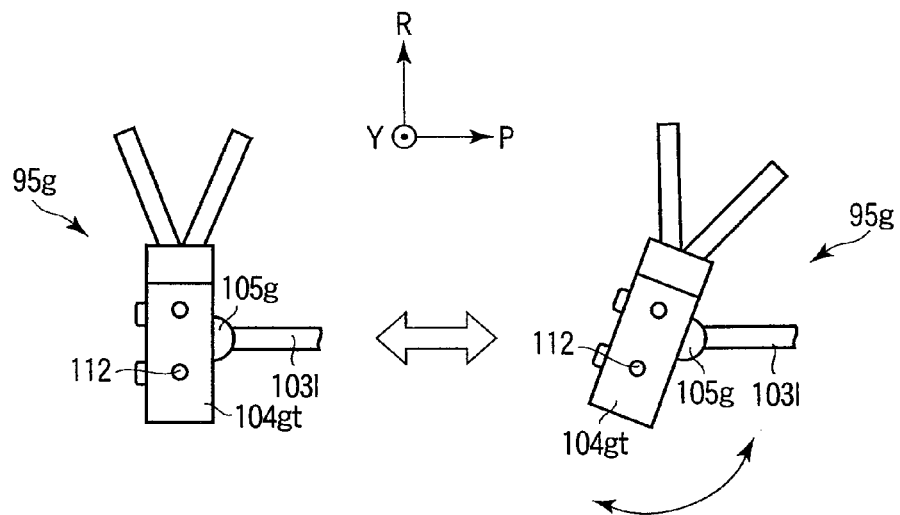
F I G. 16
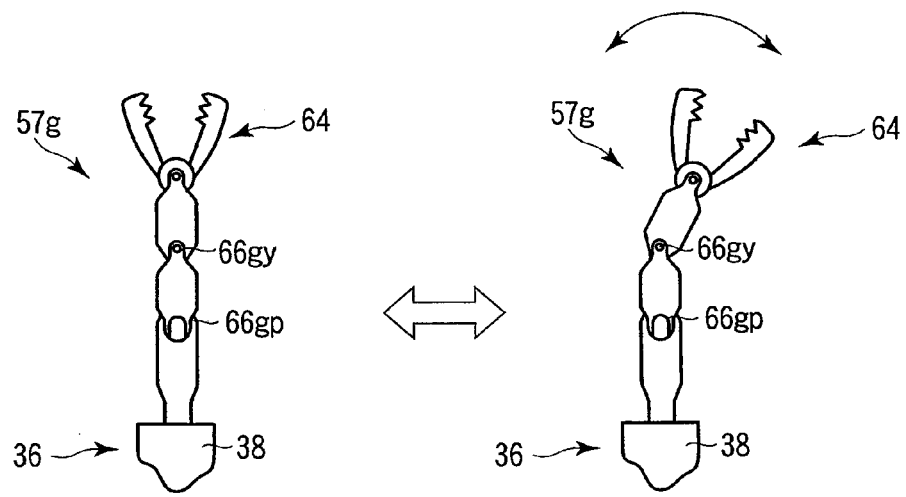
F I G. 17

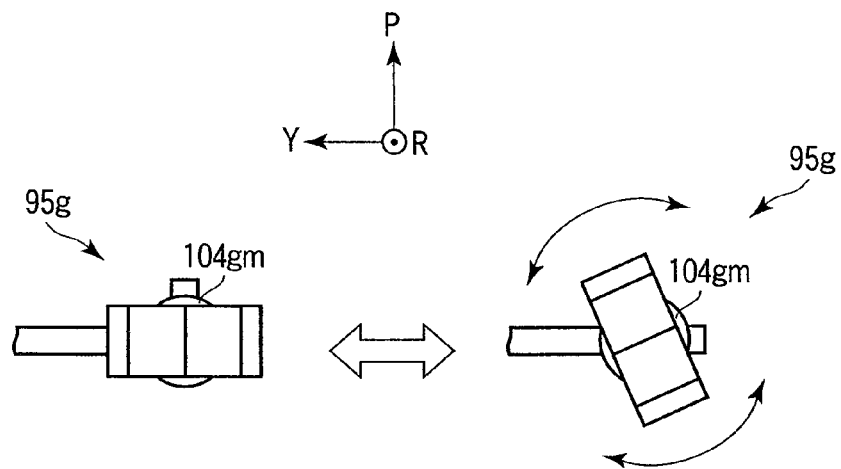
F I G. 20
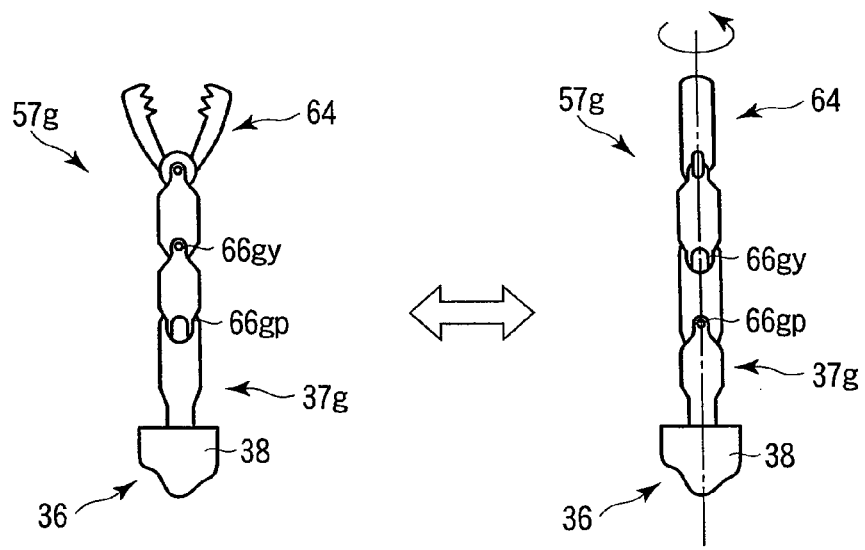
F I G. 21

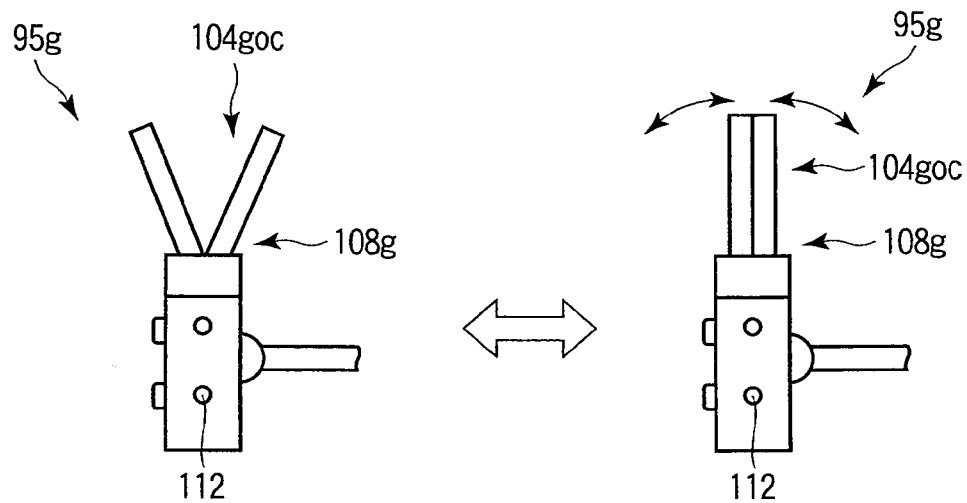
F I G. 22
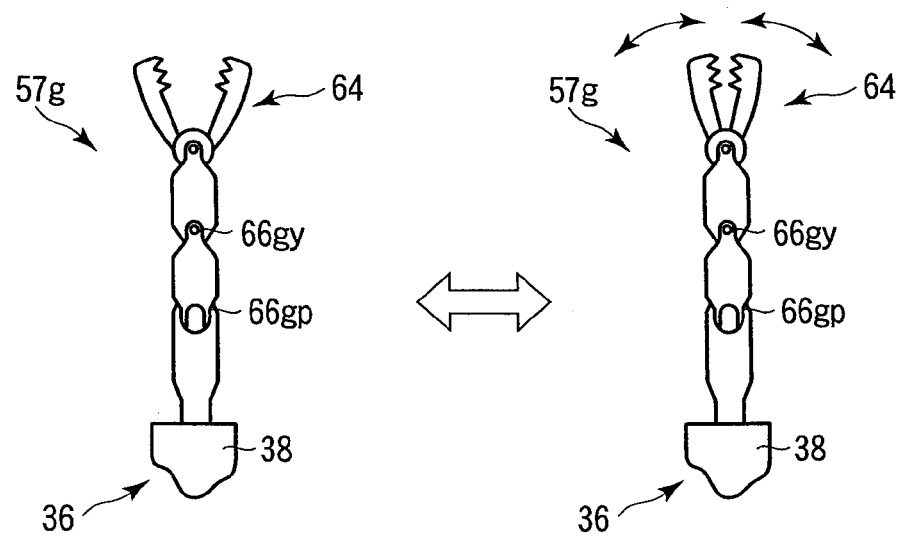
F I G. 23

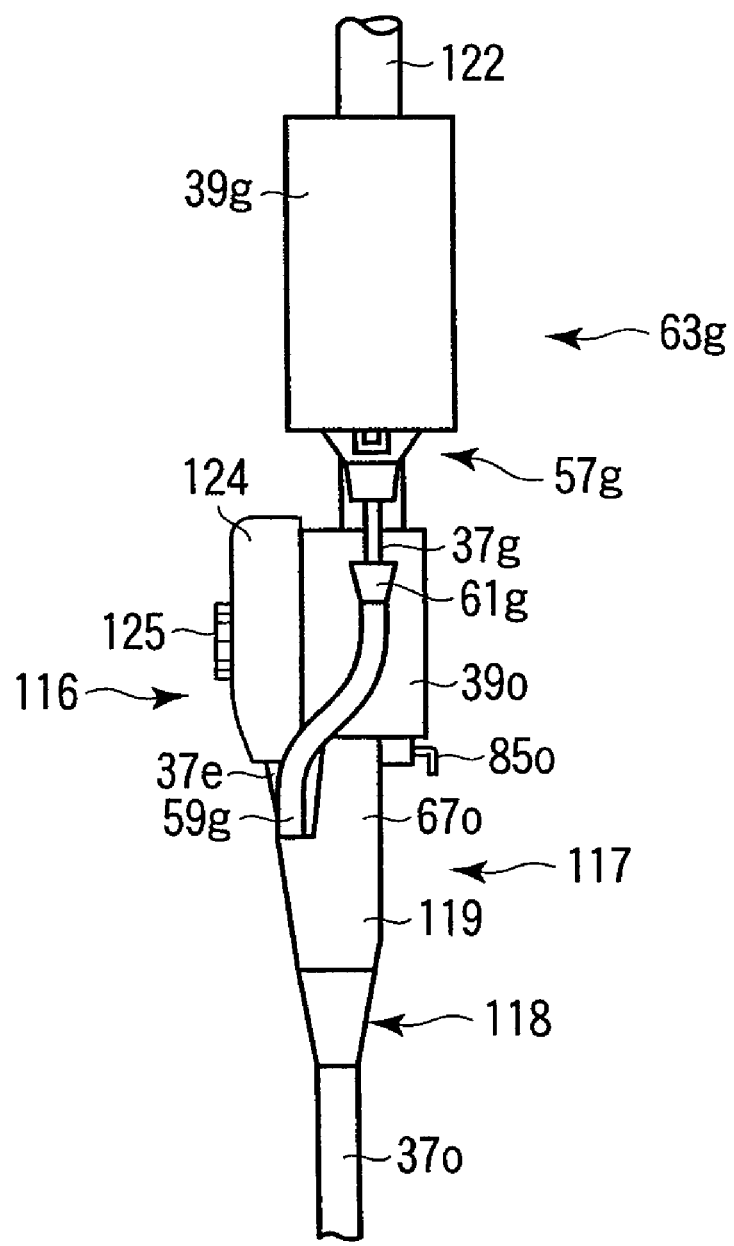
F I G. 30

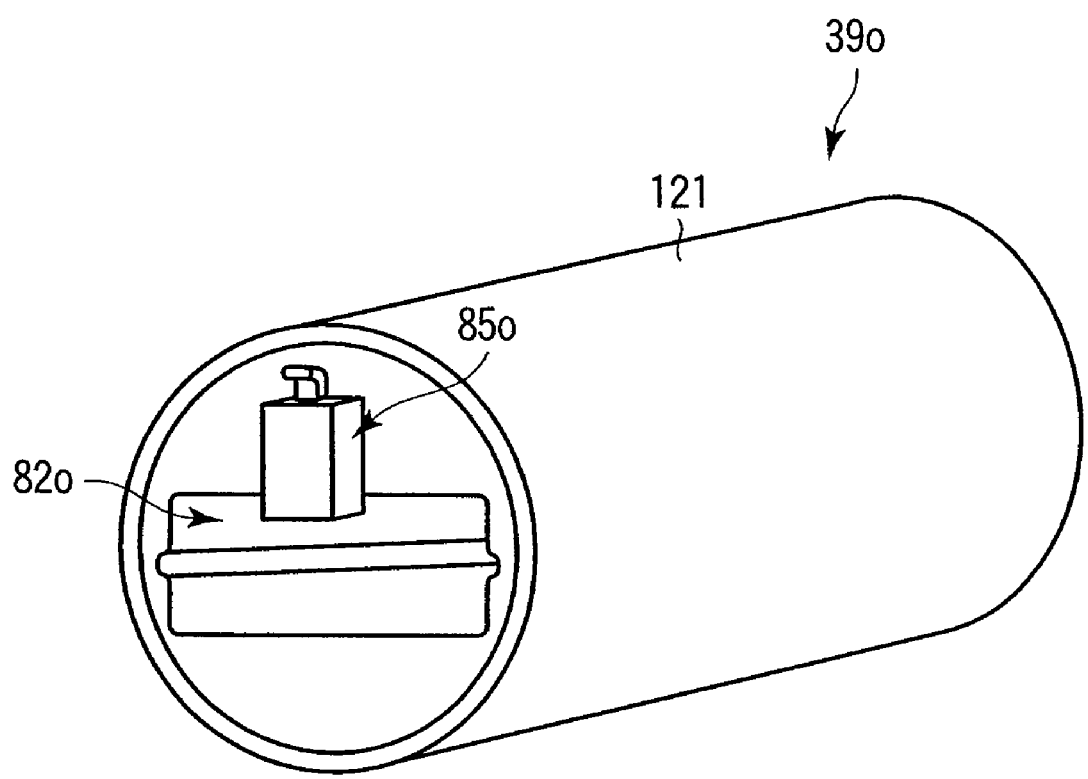
F I G. 32

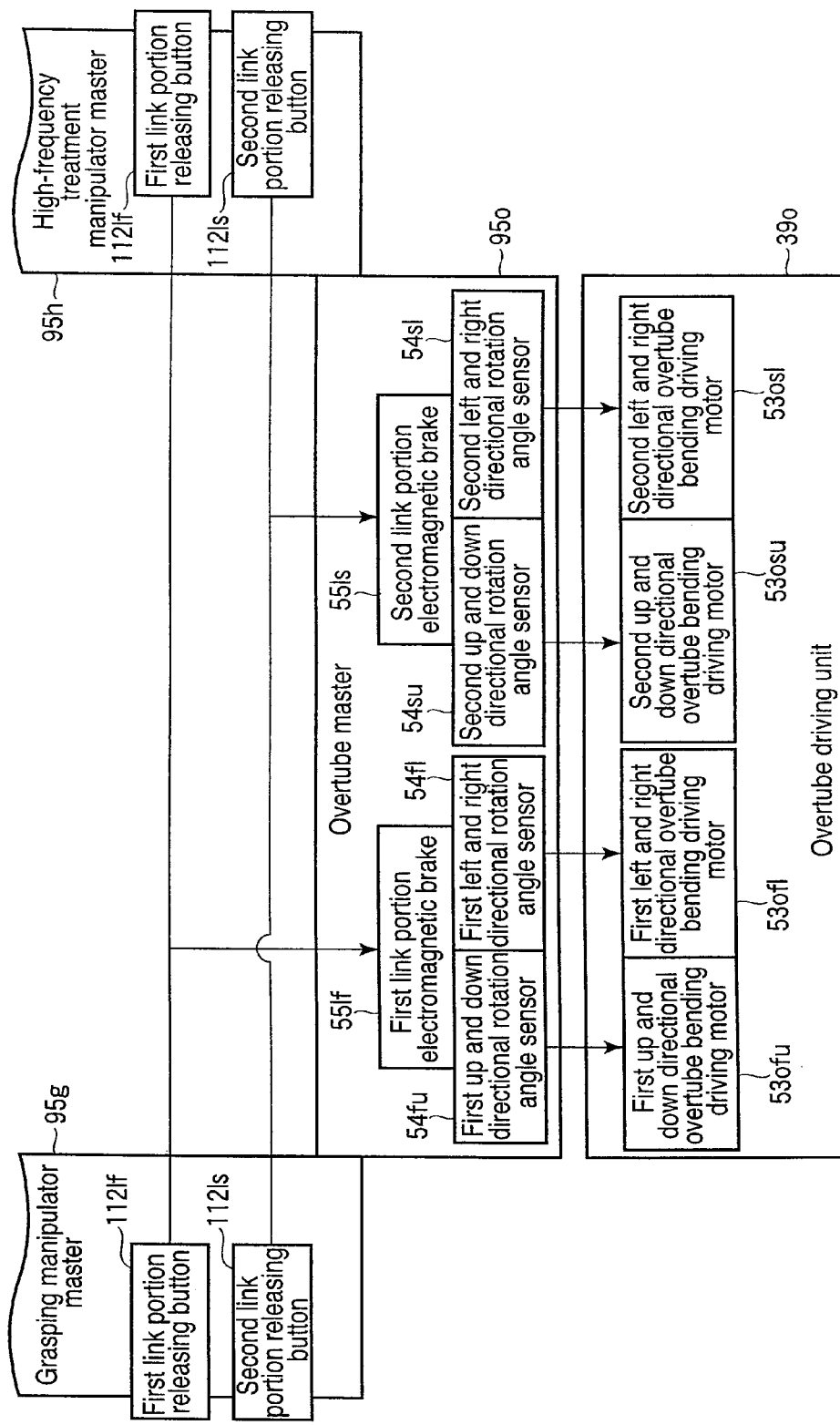
F I G. 33

MEDICAL SYSTEM

CROSS-REFERENCE TO RELATED APPLICATIONS

This is a Continuation Application of PCT Application No. PCT/JP2009/067803, filed Oct. 14, 2009, which was published under PCT Article 21(2) in Japanese.

This application is based upon and claims the benefit of priority from prior Japanese Patent Application No. 2008-292163, filed Nov. 14, 2008, the entire contents of which are incorporated herein by reference.

BACKGROUND OF THE INVENTION

1. Field of the Invention

The present invention relates to a medical system wherein an insertion slave apparatus and a treatment slave apparatus are used together with each other, and the insertion slave apparatus is operated by an insertion master portion and the treatment slave apparatus is operated by a treatment master portion.

2. Description of the Related Art

In Jpn. Pat. Appln. KOKAI Publication No. 2007-185385, an electrical bending endoscope is disclosed as an insertion slave apparatus. The electrical bending endoscope includes an insertion portion being long and configured to be inserted into the body. An endoscope bending portion is provided in the distal end portion of the insertion portion and configured to be actuated to be bent. A driving unit is coupled to the proximal end portion of the insertion portion, and an actuation portion is built into the driving unit and configured to actuate the endoscope bending portion to be bent. The driving unit is connected to a control unit through the universal cord, and an operation portion is connected to the control unit through a connecting cord. When the operation portion is operated, the actuation portion is actuated, and then, the endoscope bending portion is actuated to be bent.

In Jpn. Pat. Appln. KOKAI Publication No. 8-173442, a master-slave manipulator is disclosed as a treatment slave apparatus. The master-slave manipulator includes a middle axial portion being elongated and configured to be inserted into the body. A slave manipulator portion is coupled to the distal end portion of the middle axial portion and configured to grasp an object of treatment. On the other hand, a master manipulator portion is coupled to the proximal end portion of the middle axial portion. When the master manipulator portion is operated, the slave manipulator portion is actuated.

BRIEF SUMMARY OF THE INVENTION

In an aspect of the present invention, a medical system includes: an insertion slave apparatus configured to be inserted into a body; a treatment slave apparatus configured to be inserted into the body together with the insertion slave apparatus and configured to be used together with the insertion slave apparatus to treat an object of treatment; an insertion master portion having a similar figure to the insertion slave apparatus and including a movable portion configured to be moved, wherein the insertion slave apparatus is configured to perform following actuation according to operation input to the insertion master portion; a treatment master portion configured to be operated by an operator, wherein the treatment slave apparatus is configured to perform following actuation according to operation input to the treatment master portion; and a connecting portion coupling the insertion master portion and the treatment master portion to each other, wherein the movable portion is configured to be moved through the connecting portion to operate the insertion master portion by holding and operating the treatment master portion.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a side view showing the proximal end portions of an endoscope apparatus and a manipulator apparatus according to the first embodiment of the present invention;

FIG. 10 is a block diagram showing a control system of the endoscope apparatus in the medical system according to the first embodiment of the present invention;

FIG. 16 is a top view showing yaw axial rotational operation of the manipulator master according to the first embodiment of the present invention;

FIG. 17 is a top view showing yaw axial rotational actuation of the manipulator according to the first embodiment of the present invention;

FIG. 20 is a front view showing roll axial rotational operation of the manipulator master according to the first embodiment of the present invention;

FIG. 21 is a top view showing roll axial rotational actuation of the manipulator according to the first embodiment of the present invention;

FIG. 22 is a top view showing opening and closing operation of the manipulator master according to the first embodiment of the present invention;

FIG. 23 is a top view showing grasping actuation of the manipulator according to the first embodiment of the present invention;

FIG. 30 is a side view showing the endoscope, the manipulator apparatus and the overtube apparatus according to the fourth embodiment of the present invention;

FIG. 32 is a perspective view showing an overtube driving unit according to the fourth embodiment of the present invention;

FIG. 33 is a block diagram showing a control system of the overtube apparatus in a medical system according to the fourth embodiment of the present invention.

DETAILED DESCRIPTION OF THE INVENTION

Figure 1:
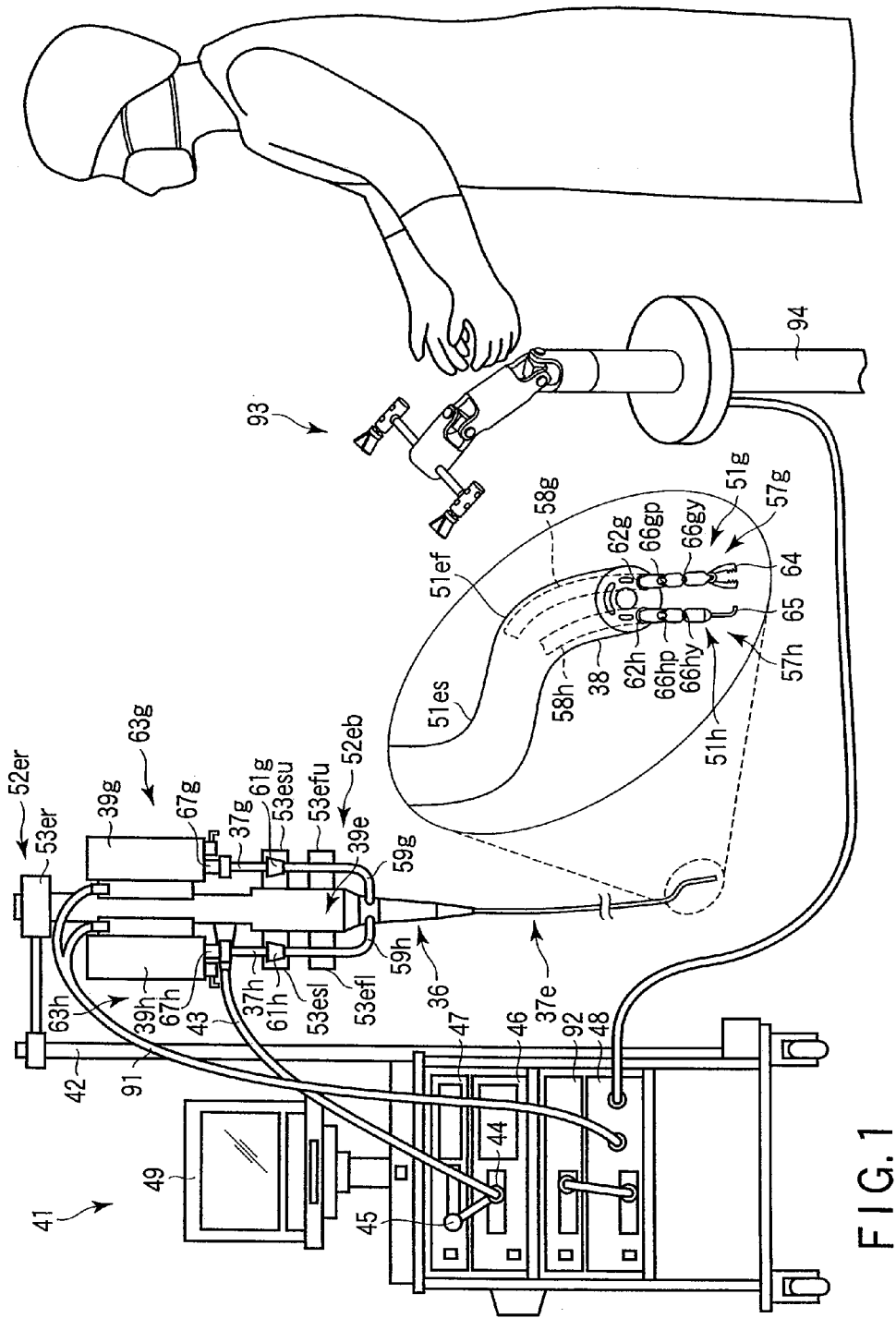
FIG. 1 is a schematic view showing a medical system according to a first embodiment of the present invention.

Hereinafter, each embodiment of the present invention will be explained referring to the drawings.

Referring to FIGS. 1 to 23, a first embodiment of the present invention will be explained.

Referring to FIGS. 1 and 2, an electrical bending endoscope 36 will be explained as an insertion slave apparatus in a medical system.

The endoscope 36 includes an endoscope insertion portion 37e being long and flexible and configured to be inserted into the body. A distal end rigid portion 38 is provided in the distal end portion of the endoscope insertion portion 37e. The proximal end portion of the endoscope insertion portion 37e is coupled to an endoscope driving unit 39e, and the endoscope driving unit 39e is held by an endoscope stand 42 of a trolley 41. A universal cord 43 extends from the endoscope driving unit 39e, and a light source connector 44 and an electrical connector 45 are provided at the extending end portion of the universal cord 43 and connected to a light source apparatus 46 and a video processor 47 of the trolley 41, respectively. Here, the video processor 47 is connected to a system controller 48. Illumination light is produced in the light source apparatus 46, transmitted to an illumination optical system in the distal end rigid portion 38 through a light guide extending between the light source connector 44 and the illumination optical system, and emitted to an object of observation from the illumination optical system. An observation image is imaged by an imaging unit in the distal end rigid portion 38 and an image signal is produced, and then, the image signal is output to the video processor 47 through an imaging cable extending between the imaging unit and the electrical connector 45, and the observation image is displayed in a monitor 49 of the trolley 41 by the video processor 47. In the distal end portion of the endoscope 36, an up and down direction and a left and right direction are determined corresponding to the up and down direction and the left and right direction in the observation image displayed in the monitor 49.

A first endoscope bending portion 51ef and a second endoscope bending portion 51es are arranged in the axial direction on the proximal end side of the distal end rigid portion 38 in the endoscope insertion portion 37e. The first and the second endoscope bending portion 51ef, 51es are configured to be actuated to be bent in the up and down direction and the left and right direction. On the other hand, an endoscope bending driving portion 52eb is provided at the distal end part of the endoscope driving unit 39e. The endoscope bending driving portion 52eb includes a first and a second up and down directional, and left and right directional endoscope bending driving motor 53efu, 53efl, 53esu, 53esl for actuating the first and the second endoscope bending portion 51ef, 51es to be bent in the up and down direction and the left and right direction. Sprockets are coupled to the endoscope bending driving motors 53efu, 53efl, 53esu and 53esl and endoscope wires are wound around the sprockets. The one end side parts and the other end side parts of the endoscope wires are inserted through the endoscope driving unit 39e and the endoscope insertion portion 37e, and coupled to the endoscope bending portions 51ef and 51es. When the sprocket is rotated by the endoscope bending driving motor 53efu, 53efl, 53esu or 53esl and the endoscope wire is actuated to be advanced and retreated, the endoscope bending portion 51ef or 51es is actuated to be bent. Furthermore, an endoscope rotational driving portion 52er is provided in the proximal end part of the endoscope driving unit 39e. The endoscope rotational driving portion 52er includes an endoscope rotational driving motor 53er. The endoscope rotational driving portion 52er is configured to actuate the whole endoscope 36 to be rotated about the central axis of the endoscope 36.

Moreover, a grasping instrument channel 58g and a high-frequency treatment instrument channel 58h extend through the endoscope insertion portion 37e, and a grasping manipulator 57g and a high-frequency treatment manipulator 57h are inserted through the grasping instrument channel 58g and the high-frequency treatment instrument channel 58h, respectively. The proximal end portions of the instrument channels 58g and 58h are connected to instrument guide pipes 59g and 59h in the proximal end portion of the endoscope insertion portion 37e. Instrument insertion openings 61g and 61h are provided at the extending end portions of the instrument guide pipes 59g and 59h and the manipulators 57g and 57h are configured to be inserted into the instrument insertion openings 61g and 61h. On the other hand, the distal end portions of the instrument channels 58g and 58h are connected to instrument protrusion openings 62g and 62h in the distal end rigid portion 38, and the manipulators 57g and 57h are configured to protrude from the instrument protrusion openings 62g and 62h.

Here, a direction of a field of view of the endoscope 36 and opening directions of the instrument protrusion openings 62g and 62h are substantially parallel to the centrally axial direction of the axial direction of the endoscope 36 and substantially parallel to one another. The grasping instrument protrusion opening 62g is arranged on the left side and the high-frequency treatment instrument protrusion opening 62h is arranged on the right side on the basis of the field of view of observation of the endoscope 36.

Referring to FIGS. 1 and 3 to 8, manipulator apparatuses 63g and 63h will be explained as treatment slave apparatuses. The manipulator apparatuses 63g and 63h are formed by the manipulators 57g and 57h and manipulator driving units 39g and 39h.

Figure 3:
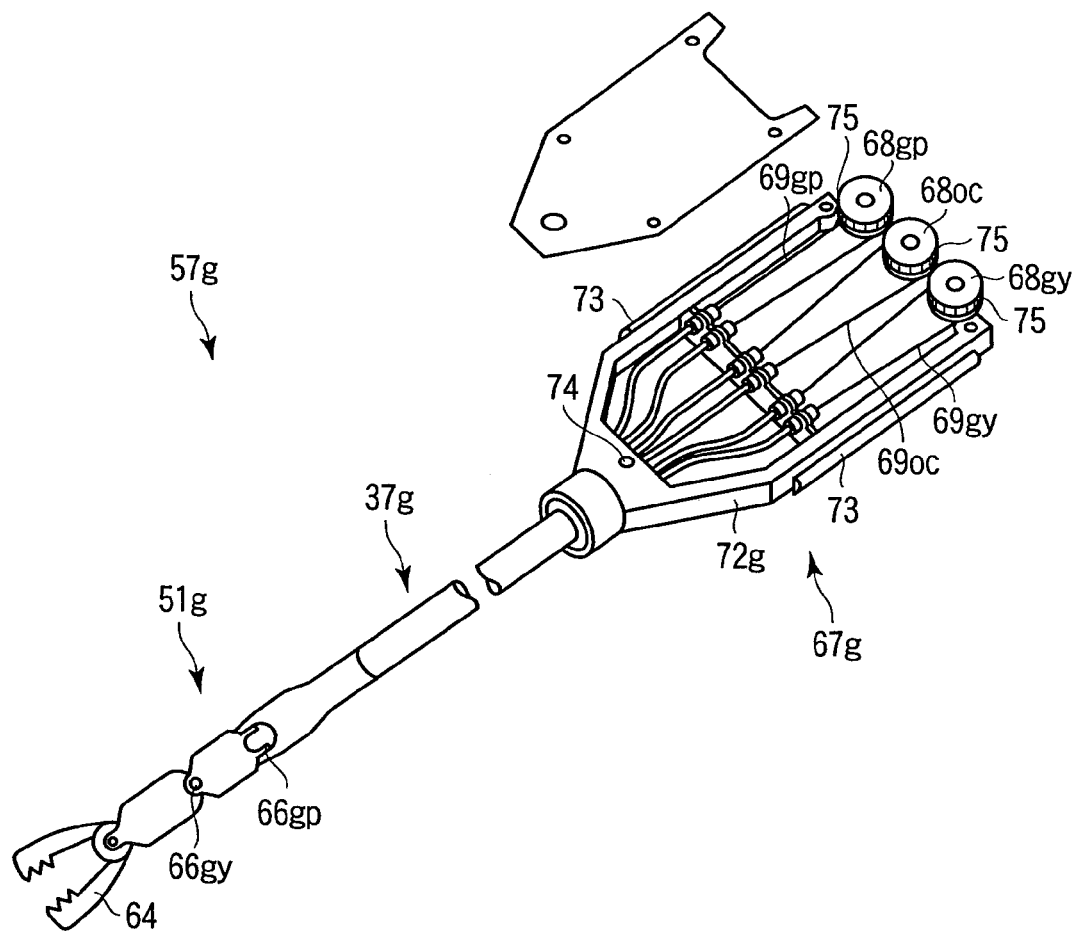
FIG. 3 is an exploded perspective view showing a grasping manipulator according to the first embodiment of the present invention.
Figure 4:
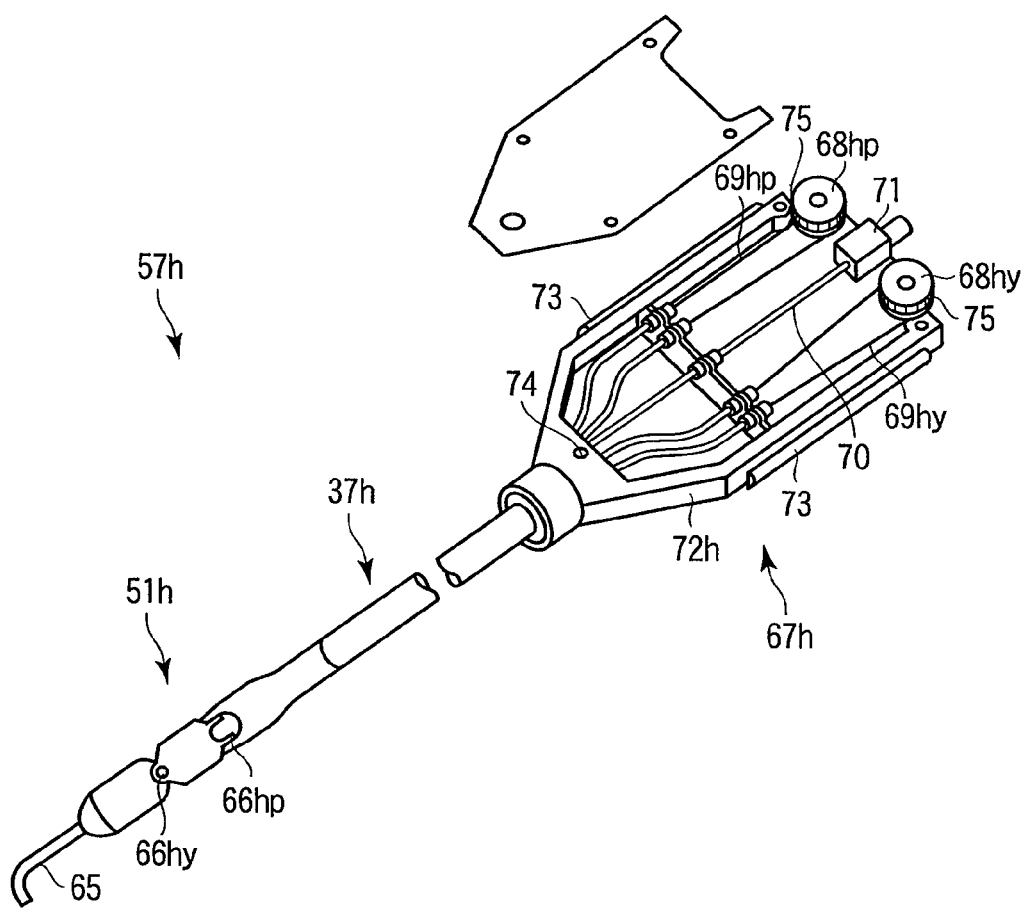
FIG. 4 is an exploded perspective view showing a high-frequency treatment manipulator according to the first embodiment of the present invention.
Figure 5:
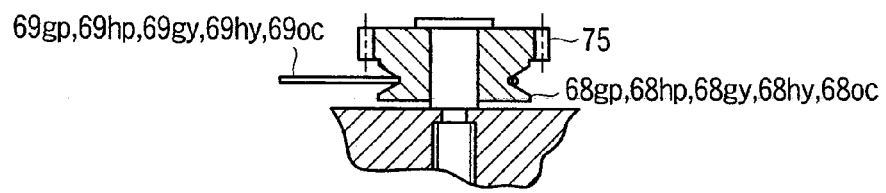
FIG. 5 is a cross-sectional view showing a pulley according to the first embodiment of the present invention.

Referring to FIGS. 3 to 5, the manipulators 57g and 57h of the manipulator apparatuses 63g and 63h include manipulator insertion portions 37g and 37h being long and flexible and configured to be inserted through the instrument channels 58g and 58h of the endoscope 36. In the grasping manipulator 57g, a grasping portion 64 is provided at the distal end portion of the manipulator insertion portion 37g. The grasping portion 64 is configured to be actuated to be opened and closed to grasp living tissue. In the high-frequency treatment manipulator 57h, a high-frequency electrode 65 is provided at the distal end portion of the manipulator insertion portion 37h. A high-frequency current is adapted to flow through the high-frequency electrode 65 and the high-frequency electrode 65 is configured to come in contact with living tissue to incise it with the high-frequency current. Manipulator bending portions 51g and 51h are provided on the proximal end sides of the grasping portion 64 and the high-frequency electrode 65, respectively, and configured to be actuated to be bent. In the manipulator bending portions 51g and 51h, pitch joint portions 66gp and 66hp are provided on the distal end sides and yaw joint portions 66gy, 66hy are provided on the proximal end sides. The grasping portion 64 and the high-frequency electrode 65 are moved in the pitch directions and the yaw directions by rotational actuations of the pitch joint portions 66gp and 66hp and the yaw joint portions 66gy and 66hy, respectively.

Cassette-like manipulator driving connecting portions 67g and 67h are coupled to the proximal end portions of the manipulator insertion portions 37g and 37h. Pitch axial rotational pulleys 68gp and 68hp and yaw axial rotational pulleys 68gy and 68hy are provided in the manipulator driving connecting portions 67g and 67h. Pitch axial rotational manipulator wires 69gp and 69hp and yaw axial rotational manipulator wires 69gy and 69hy are wound around the pitch axial rotational pulleys 68gp and 68hp and the yaw axial rotational pulleys 68gy and 68hy, respectively. The one end side parts and the other end side parts of the pitch axial rotational manipulator wires 69gp and 69hp and the yaw axial rotational manipulator wires 69gy and 69hy are inserted through the manipulator driving connecting portions 67g and 67h and the manipulator insertion portions 37g and 37h, and coupled to the pitch joint portions 66gp and 66hp and the yaw joint portions 66gy and 66hy, respectively. When the pitch axial rotational pulley 68gp or 68hp or the yaw axial rotational pulley 68gy or 68hy is rotated and the pitch axial rotational manipulator wire 69gp or 69hp or the yaw axial rotational manipulator wire 69gy or 69hy is actuated to be advanced and retreated, the pitch joint portion 66gp or 66hp or the yaw joint portion 66gy or 66hy is actuated to be rotated. Furthermore, in the grasping manipulator 57g, an opening and closing pulley 68oc and an opening and closing manipulator wire 69oc are used. When the opening and closing pulley 68oc is rotated and the opening and closing manipulator wire 69oc is actuated to be advanced and retreated, the grasping portion 64 is actuated to be opened and closed. On the other hand, in the high-frequency manipulator 57h, the distal end portion of a current cable 70 is coupled to the inner end portion of the high-frequency electrode 65. The current cable 70 is inserted through the manipulator insertion portion 37h, put into the manipulator driving connecting portion 67h, and connected to an electrical contact portion 71.

Moreover, guide convex portions 73 and click holes 74 are formed in connecting portion housings 72g and 72h of the manipulator driving connecting portions 67g and 67h as connecting mechanisms of the manipulators 57g and 57h and the manipulator driving units 39g and 39h. Furthermore, pulley spur gears 75 are formed in the pulleys 68oc, 68gp, 68gy, 68hp and 68hy. Moreover, in the high-frequency manipulator 57h, the electrical contact portion 71 protrudes from the connecting portion housing 72h.

Figure 6:
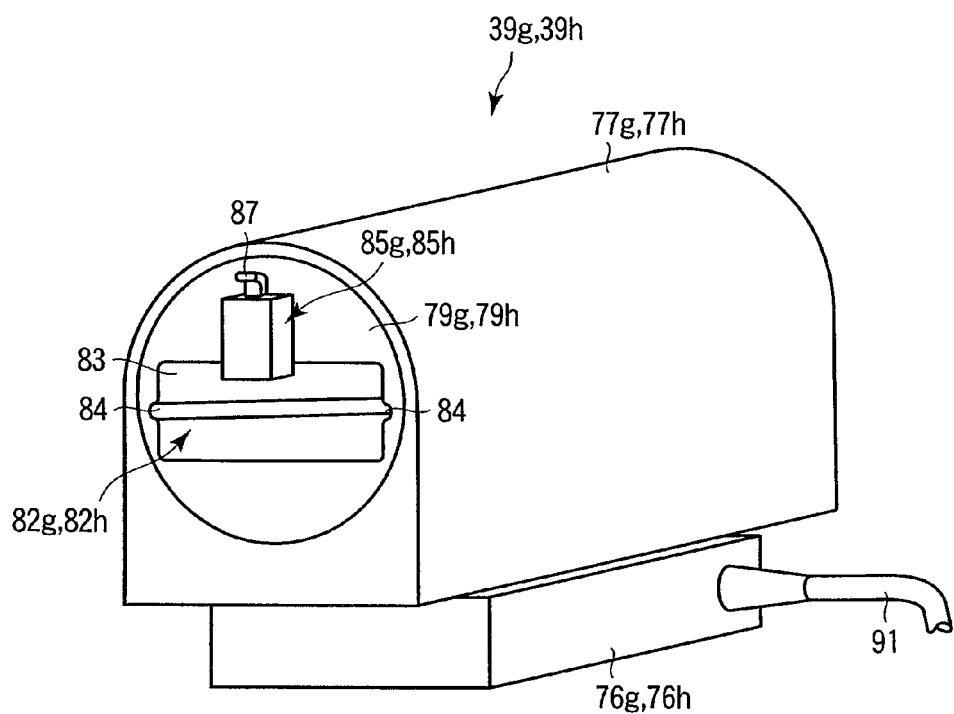
FIG. 6 is a perspective view showing a manipulator driving unit according to the first embodiment of the present invention.
Figure 7:
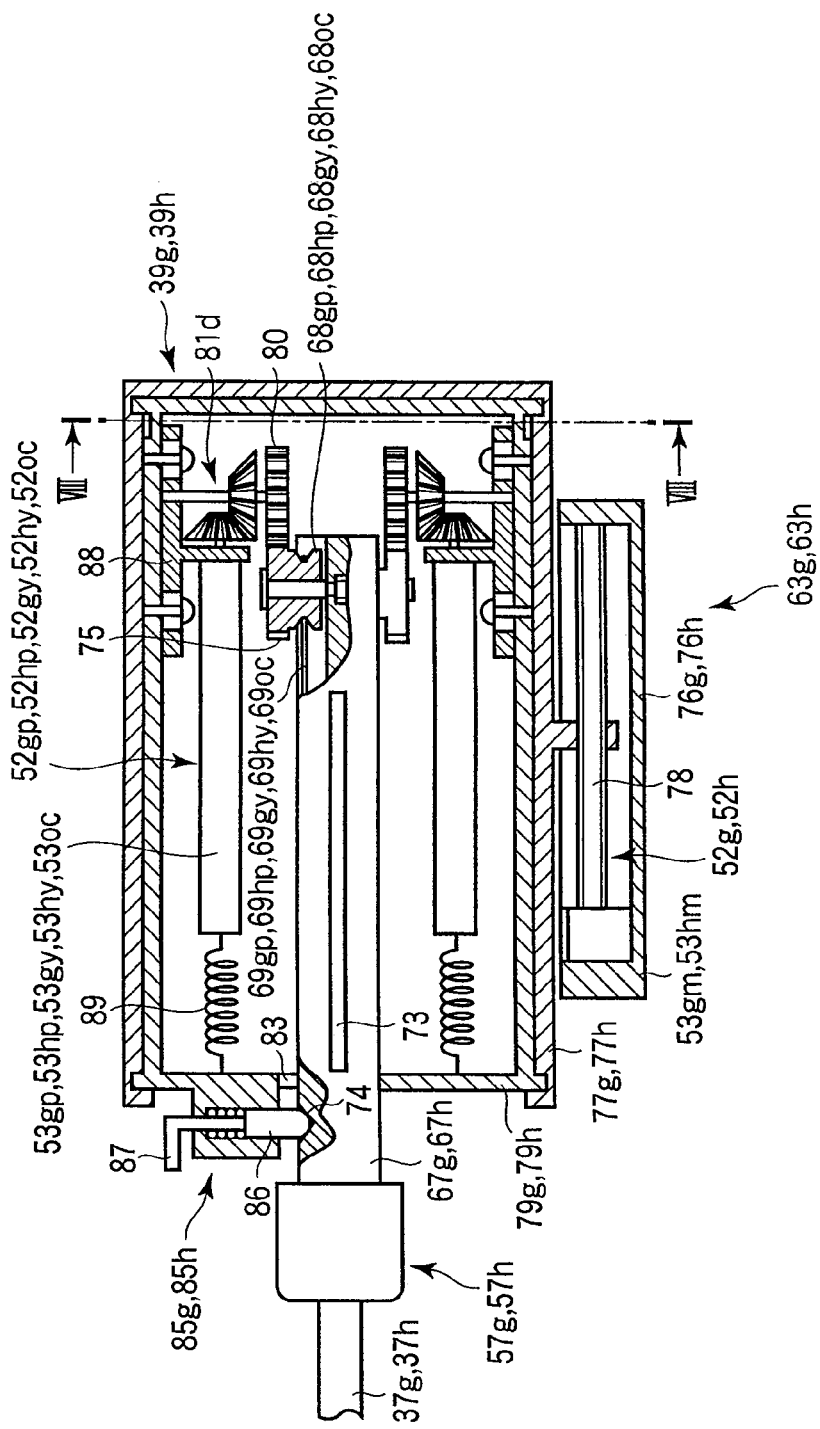
FIG. 7 is a longitudinally cross-sectional view showing the manipulator driving unit according to the first embodiment of the present invention.
Figure 8:
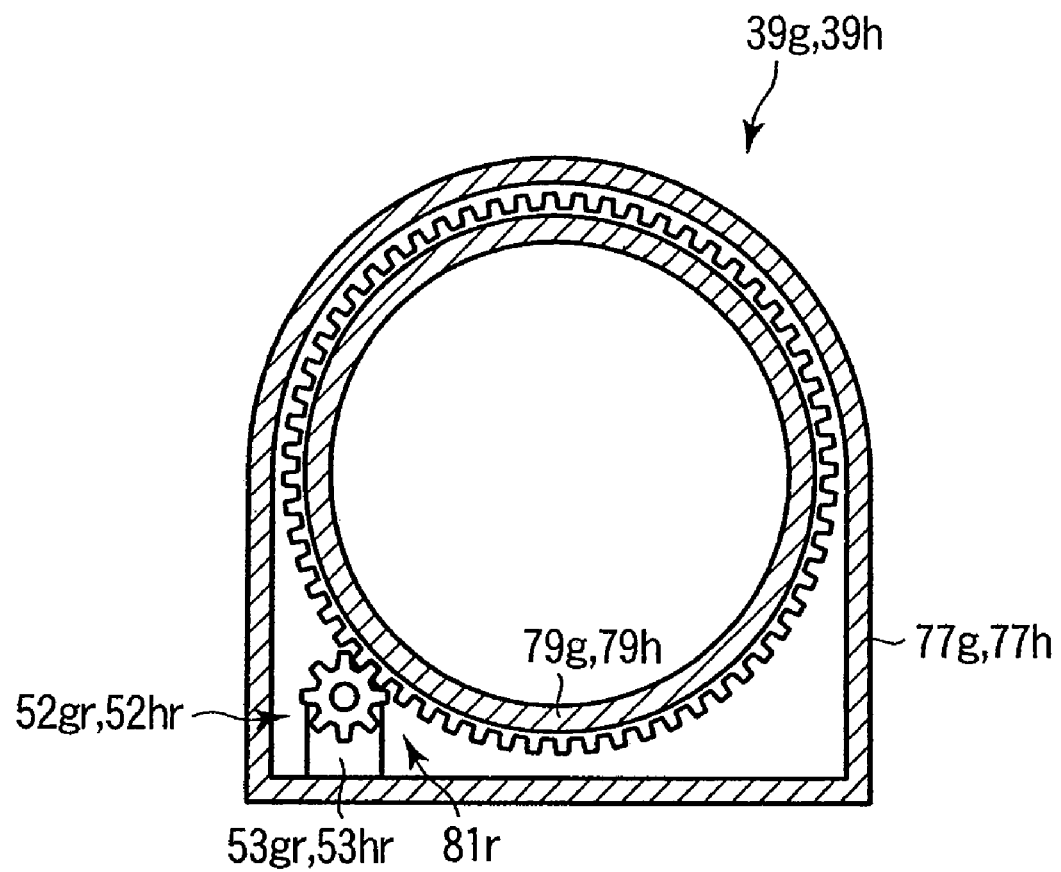
FIG. 8 is a transversely cross-sectional view showing the manipulator driving unit according to the first embodiment of the present invention along a line VIII-VIII in FIG. 7.

Referring to FIGS. 6 to 8, the manipulator driving units 39g and 39h include base portions 76g and 76h. Advancing and retreating portions 77g and 77h are provided upon the base portions 76g and 76h. The advancing and retreating portions 77g and 77h are configured to be actuated to be advanced and retreated in the central axial direction of the manipulator driving units 39g and 39h relative to the base portions 76g and 76h by advancing and retreating driving portions 52gm and 52hm built into the base portions 76g and 76h. In the advancing and retreating driving portions 52gm and 52hm, advancing and retreating driving motors 53gm and 53hm and feed screw mechanisms 78 are used.

Manipulator rotational portions 79g and 79h are housed within the advancing and retreating portions 77g and 77h. The manipulator rotational portions 79g and 79h are configured to be rotated about the central axis of the manipulator driving units 39g and 39h relative to the advancing and retreating portions 77g and 77h by manipulator rotational driving portions 52gr and 52hr built into the advancing and retreating portions 77g and 77h. Manipulator rotational driving motors 53gr and 53hr and rotational gear mechanisms 81r are used in the manipulator rotational driving portions 52gr and 52hr.

Manipulator connecting portion housing portions 82g and 82h are formed in the manipulator rotational portions 79g and 79h and are configured to house coaxially the manipulator driving connecting portions 67g and 67h of the manipulators 57g and 57h. Connecting portion insertion openings 83 are formed in the one end portions in the central axial direction of the manipulator rotational portions 79g and 79h and the manipulator driving connecting portions 67g and 67h are configured to be inserted into the manipulator connecting portion housing portions 82g and 82h through the connecting portion insertion openings 83. Guide concave portions 84 are formed in the manipulator connecting portion housing portions 82g and 82h and configured to guide convex portions 73 of the manipulator driving connecting portions 67g and 67h. Moreover, manipulator connecting portion engaging portions 85g and 85h are provided in the one end surface portions of the manipulator rotational portions 79g and 79h. When the manipulator driving connecting portion 67g or 67h is inserted into the manipulator connecting portion housing portion 82g or 82h, a click pin 86 of the manipulator connecting portion engaging portion 85g or 85h is engaged with the click hole 74 of the manipulator driving connecting portion 67g or 67h, and the manipulator driving connecting portion 67g or 67h is held relative to the manipulator rotational portion 79g or 79h. When a releasing lever 87 of the manipulator connecting portion engaging portion 85g or 85h is operated, the click pin 86 and the click hole 74 are disengaged from each other, the manipulator driving connecting portion 67g or 67h is released relative to the manipulator rotational portion 79g or 79h, and the manipulator driving connecting portion 67g or 67h can be extracted from the manipulator connecting portion housing portion 82g or 82h.

Moreover, pitch axial rotational driving portions 52gp and 52gy and yaw axial rotational driving portions 52hp and 52hy are provided within the manipulator rotational portions 79g and 79h. Furthermore, an opening and closing driving portion 52oc is provided in the grasping manipulator driving unit 39g. Pitch axial rotational driving motors 53gp and 53hp and driving gear mechanisms 81d are used in the pitch axial rotational driving portions 52gp and 52gy, yaw axial rotational driving motors 53gy and 53hy and driving gear mechanisms 81d are used in the yaw axial rotational driving portions 52hp and 52hy, and an opening and closing driving motor 53oc and a driving gear mechanism 81d are used in the opening and closing driving portion 52oc. When the manipulator driving connecting portion 67g or 67h is inserted into and extracted from the manipulator connecting portion housing portion 82g or 82h, the pulley spur gears 75 of the pulleys 68oc, 68gp, 68gy or 68hp, 68hy of the manipulator driving connecting portion 67g or 67h are engaged with and separated from the driving spur gears 80 at the terminal ends on the driven sides of the driving gear mechanisms 81d, respectively. Here, the driving motors 53oc, 53gp, 53gy, 53hp and 53hy and the driving gear mechanisms 81d are supported by support base portions 88, and the support base portions 88 are supported so as to advance and retreat in the insertion and extraction direction of the manipulator driving connecting portions 67g and 67h. The driving motors 53oc, 53gp, 53gy, 53hp and 53hy, the driving gear mechanisms 81d and the support base portions 88 are urged in the opposite directions to the insertion directions of the manipulator driving connecting portions 67g and 67h by elastic members 83. Therefore, when the manipulator driving connecting portion 67g or 67h is inserted into the manipulator connecting portion housing portion 82g or 82h and the pulley spur gears 75 are engaged with the driving spur gears 80, the driving spur gears 80 and the pulley spur gears 75 can be surely engaged.

Moreover, an electrical contact receiving portion which is not shown is provided within the manipulator rotational portion 79h of the high-frequency treatment manipulator driving unit 39h. In the high-frequency treatment manipulator apparatus 63h, when the manipulator driving connecting portion 67h is inserted into and extracted from the manipulator connecting portion housing portion 82h, the electrical contact portion 71 is connected to and separated from the electrical contact receiving portion.

When the manipulator 57g or 57h is connected to the manipulator driving unit 39g or 39h, and then, the advancing and retreating driving motor 53gm or 53hm actuates the advancing and retreating portion 77g or 77h and the manipulator rotational portion 79g or 79h to be advanced and retreated, the whole manipulator 57g or 57h is actuated to be advanced and retreated in the centrally axial direction of the manipulator 57g or 57h, and the grasping portion 64 or the high-frequency electrode 65 of the manipulator 57g or 57h is actuated to be advanced and retreated. Moreover, when the manipulator rotation driving motor 53gr or 53hr actuates the manipulator rotational portion 79g or 79h to be rotated, the whole manipulator 57g or 57h is actuated to be rotated about the central axis of the manipulator 57g or 57h, and the grasping portion 64 or the high-frequency electrode 65 of the manipulator 57g or 57h is actuated to be rotated. When the opening and closing driving motor 53oc, the pitch axial rotational driving motor 53gp or 53hp or the yaw axial rotational driving motor 53gy of 53hy actuates the pulley 68oc, 68gp 68hp, 68gy or 68hy of the manipulator 57g to be rotated through the driving gear mechanism 81d, the grasping portion 64 is actuated to be opened and closed or the joint portion 66gp, 66hp, 66gy or 66hy is actuated to be rotated.

Referring to FIG. 1 again, the manipulator driving units 39g and 39h of the grasping manipulator apparatus 63g and the high-frequency treatment manipulator apparatus 63hs are coupled and fixed to the middle part of the endoscope driving unit 39e. The endoscope 36 and both the manipulator apparatuses 63g and 63h are configured to be integrally actuated to be rotated by the endoscope rotational driving portion 52er. The manipulator driving units 39g and 39h are connected to the system controller 48 through a compound cord 91, and the high-frequency treatment manipulator driving unit 39h is connected to the high-frequency power apparatus 92.

Referring to FIGS. 1 and 9 to 11, a master apparatus 93 will be explained.

The master apparatus 93 is connected to the system controller 48. The master apparatus 93 stands on a master apparatus stand 94 configured to be set on a floor.

Figure 9:
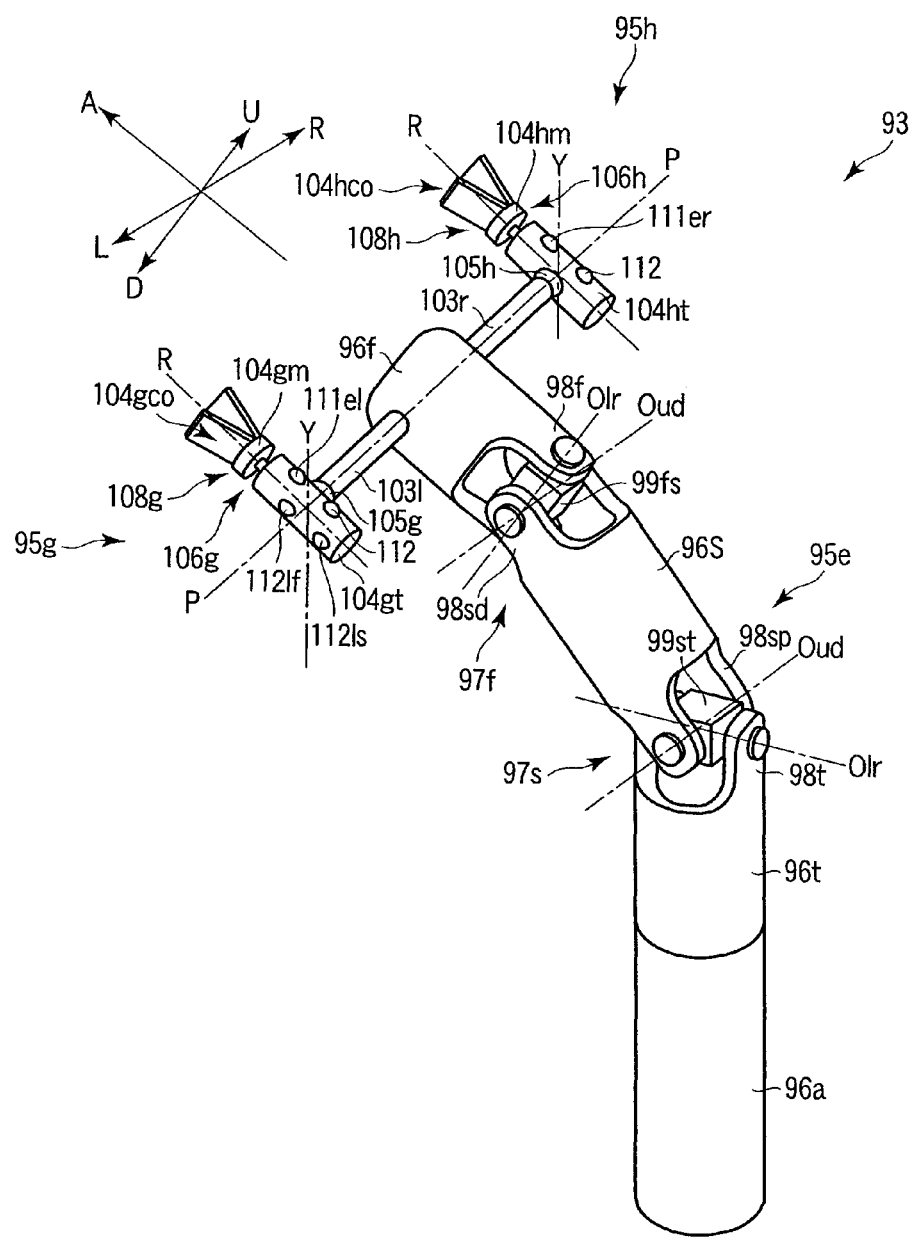
FIG. 9 is a perspective view showing a master apparatus according to the first embodiment of the present invention.
Figure 11:
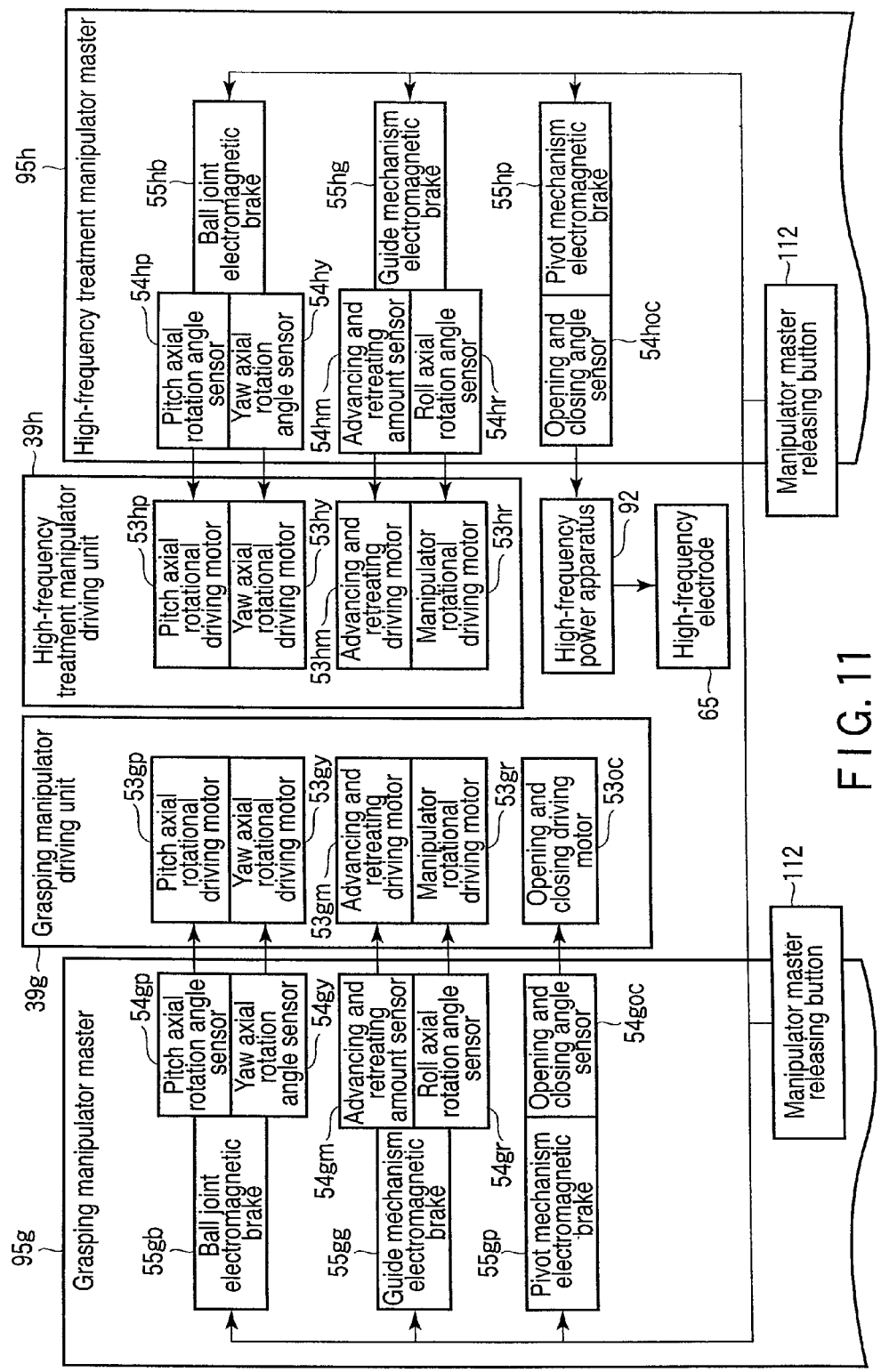
FIG. 11 is a block diagram showing a control system of the manipulator apparatus in the medical system according to the first embodiment of the present invention.
Figure 12:
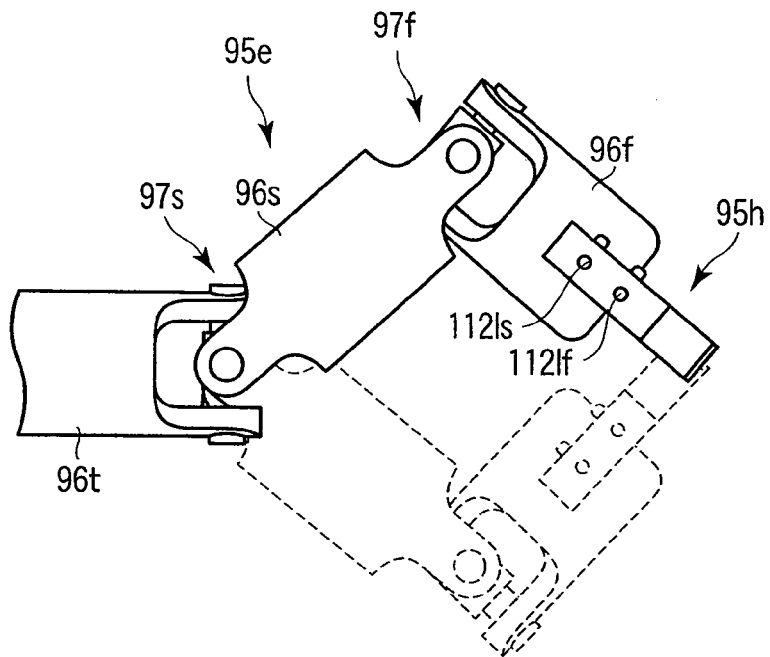
FIG. 12 is a side view showing bending operation of an endoscope master according to the first embodiment of the present invention.
Figure 13:
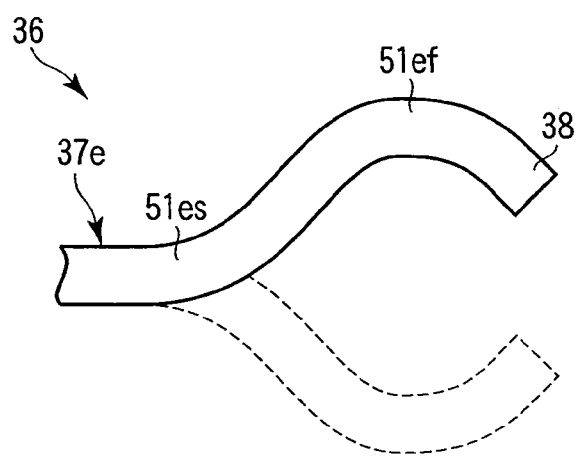
FIG. 13 is a side view showing bending actuation of an endoscope according to the first embodiment of the present invention.
Figure 14:
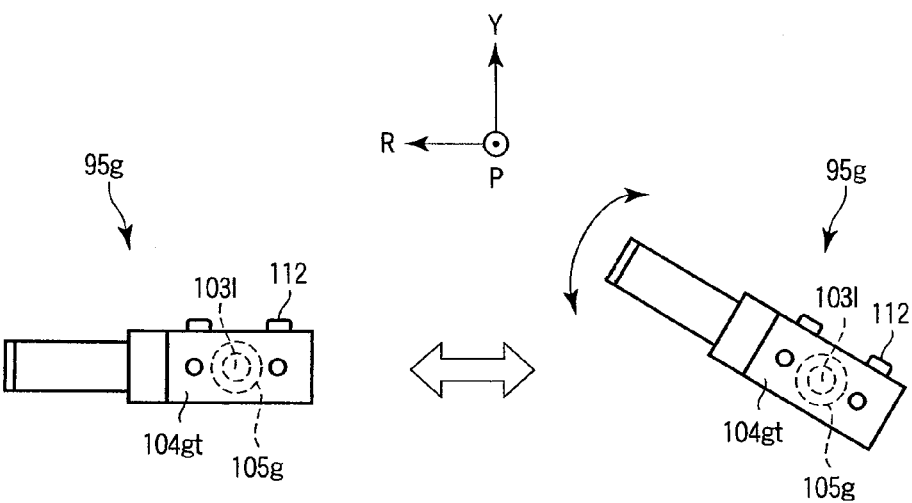
FIG. 14 is a view showing pitch axial rotational operation of a manipulator master according to the first embodiment of the present invention.
Figure 15:
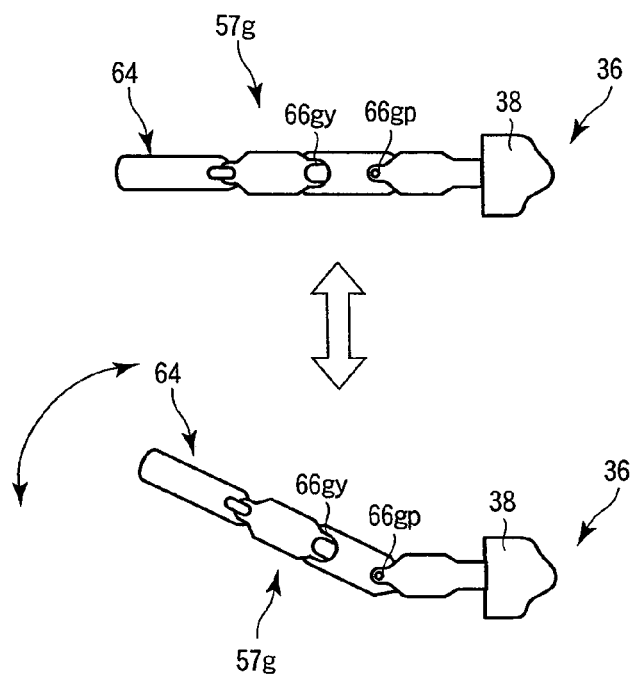
FIG. 15 is a side view showing pitch axial rotational actuation of a manipulator according to the first embodiment of the present invention.
Figure 18:
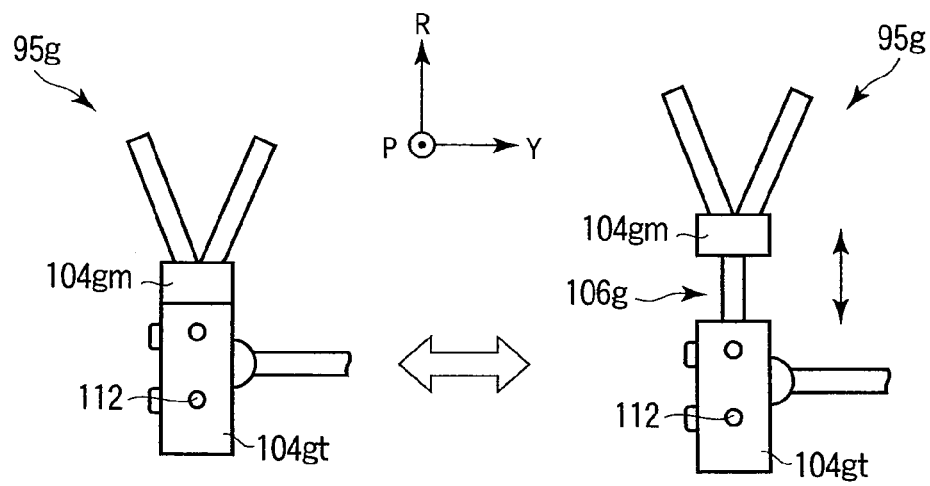
FIG. 18 is a top view showing advancing and retreating operation of the manipulator master according to the first embodiment of the present invention.
Figure 19:
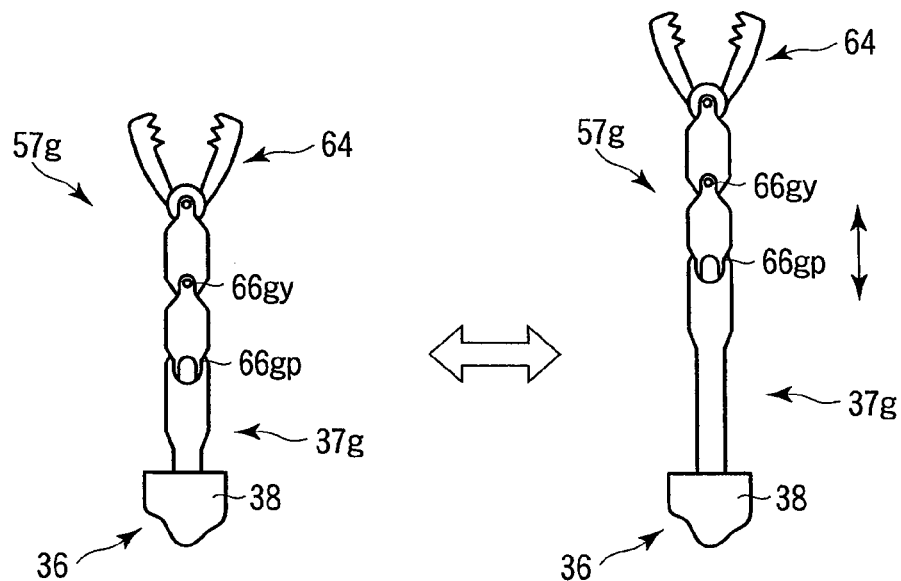
FIG. 19 is a top view showing advancing and retreating actuation of the manipulator according to the first embodiment of the present invention.

The master apparatus 93 includes an endoscope master 95e as an insertion master portion. The endoscope master 95e has a similar figure to the distal end portion of the endoscope 36. That is, in the endoscope master 95e, a first arm portion 96f, a second arm portion 96s and a third arm portion 96t which are circular cylindrical are provided from the distal end side to the proximal end side, and the third arm portion 96t is attached to the master apparatus stand 94 through an attachment arm portion 96a. Here, in the first, the second, the third and the attachment arm portion 96f, 96s, 96t, 96a, two directions which are orthogonal to the central axis and orthogonal to each other are referred to as an up and down direction and an left and right direction, respectively. In the normal arrangement, the first arm portion 96f, the second are portion 96s, the third arm portion 96t and the attachment arm portion 96a are arranged in a straight line, and the up and down directions of the first arm portion 96f, the second arm portion 96s, the third arm portion 96t and the attachment arm portion 96a substantially agree with one another and the left and right directions of those substantially agree with one another. In FIG. 9, arrows A, U, D, R and L refer to the centrally axial direction, the up direction, the down direction, the right direction and the left direction of the first arm portion 96f, respectively. A first link portion 97f functioning as a universal joint is interposed between the first arm portion 96f and the second arm portion 96s and the second link portion 97s functioning as a universal joint is interposed between the second arm portion 96s and the third arm portion 96t. The arm portions 96f and 96s on the distal end sides are rotatable in the up and down directions and the left and right directions relative to the arm portions 96s and 96t on the proximal end sides by the link portions 97f and 97s. That is, in the first link portion 97f, both tongue portions 98f protrude in the axial direction at the proximal end portion of the first arm portion 96f at the up position and the down position, respectively. A rotational block 99fs is arranged between both the tongue portions 98f, and both the tongue portions 98f are pivotally attached to the rotational block 99fs. Both the tongue portions 98f are rotatable relative to the rotational block 99fs about a left and right directional rotational axis Olr orthogonal to the central axis of the first arm portion 96f and extending in the up and down direction. On the other hand, both tongue portions 98sd protrude in the axial direction at the distal end portion of the second arm portion 96s at the left position and the right position, respectively. The rotational block 99fs is arranged between both the tongue portions 98sd and pivotally attached to both the tongue portions 98sd. The rotational block 99fs is rotatable relative to both the tongue portions 98*sd* about an up and down directional rotational axis Oud orthogonal to the central axis of the second arm portion 96*s* and extending in the left and right direction. The second link portion 97*s* also has a similar configuration to that of the first link portion 97*f*. That is, both tongue portions 98*sp* of the proximal end portion of the second link portion 97*s* are rotatable relative to a rotational block 99*st* about an up and down directional rotational axis Oud, and the rotational block 99*st* is rotatable relative to both the tongue portions 98*t* of the distal end portion of the third link portion 97*t* about a left and right directional rotational axis Olr. Electromagnetic brakes 55*lf* and 55*ls* are provided in the link portions 97*f* and 97*s*. The electromagnetic brakes 55*lf* and 55*ls* are configured to be switched between releasing states to make the arm portions 96*f* and 96*s* on the distal end sides rotatable relative to the arm portions 96*s* and 96*t* on the proximal end sides in the up and down directions and the left and right directions, and fixing states to make the arm portions 96*f* and 96*s* on the distal end sides unrotatable relative to the arm portions 96*s* and 96*t* on the proximal end sides in the up and down directions and the left and right directions. Furthermore, a first up and down directional rotation angle sensor 54*fu*, a first left and right directional rotation angle sensor 54*fl*, a second up and down directional rotation angle sensor 54*su* and a second left and right directional rotation angle sensor 54*sl* are provided in the first link portion 97*f* and the second link portion 97*s*, respectively, and configured to detect rotation angles of the arm portions 96*f* and 96*s* on the distal end side relative to the arm portions 96*s* and 96*t* on the proximal end side in the up and down direction and the left and right direction. Encoders are used as the rotation angle sensors, which are configured to detect amounts of the rotation angles. The rotation angles detected by the first up and down directional, and first left and right directional rotation angle sensor 54*fu*, 54*fl* and the second up and down directional, left and right directional rotation angle sensor 54*su*, 54*sl* are used for control of bending actuations of the first endoscope bending portion 51*ef* and the second endoscope bending portion 51*es* of the endoscope 36 in the up and down direction and the left and right direction, respectively.

The root portions of rod-like support arms 103*l* and 103*r* are coupled to the left end portion and the right end portion of the distal end portion of the first arm portion 96*f* of the endoscope master 95*e* as connecting portions, respectively. The support arms 103*l* and 103*r* on the left side and the right side extend straight in the left direction and the right direction, respectively. Manipulator masters 95*g* and 95*h* as treatment master portions are coupled to the terminal end portions of the support arms 103*l* and 103*r*. The grasping manipulator master 95*g* is arranged on the left side and configured to be used for control of actuation of the grasping manipulator 57*g*, and the high-frequency treatment manipulator master 95*h* is arranged on the right side and configured to be used for control of actuation of the high-frequency treatment manipulator 57*h*.

The manipulator masters 95*g* and 95*h* include columnar tilting operation portions 104*gt* and 104*ht*. Ball joints 105*g*, 105*h* are interposed between the tilting operation portions 104*gt* and 104*ht* and the terminal end portions of the support arms 103*l* and 103*r*. The central axes of the tilting operation portions 104*gt* and 104*ht* form the central axes of the manipulator masters 95*g* and 95*h* and are configured to be arranged parallel to the central axes of the first arm portion 96*f* of the endoscope master 95*e* at the normal arrangement. In the manipulator masters 95*g* and 95*h*, an axis extending in the left and right direction of the first arm portion 96*f* is referred to as a pitch axis P and axes extending in the up and down direction of the first arm portion 96*f* are referred to as yaw axes Y. The tilting operation portions 104*gt* and 104*ht* are supported by the ball joints 105*g* and 105*h* so as to be rotatable about the pitch axis P and the yaw axes Y relative to the terminal end portions of the support arms 103*l* and 103*r*. Electromagnetic brakes 55*gb* and 55*hb* are provided at the ball joints 105*g* and 105*h*, and the electromagnetic brakes 55*gb* and 55*hb* are configured to be switched between releasing states to make the tilting operation portions 104*gt* and 104*ht* rotatable relative to the terminal end portions of the support arms 103*l* and 103*r*, and fixing states to make the tilting operation portions 104*gt* and 104*ht* unrotatable relative to the terminal end portions of the supports arms 103*l* and 103*r*. Moreover, pitch axial rotation angle sensors 54*gp* and 54*hp* and yaw axial rotation angle sensors 54*gy* and 54*hy* are provided at the ball joints 105*g* and 105*h* and configured to detect rotation angles of the tilting operation portions 104*gt* and 104*ht* about the pitch axis P and the yaw axes Y, respectively. The pitch axial rotation angles and the yaw axial rotation angles detected by the pitch axial rotation angle sensors 54*gp* and 54*hp* and the yaw axial rotation angle sensors 54*gy* and 54*hy* are used for control of rotational actuations of the pitch joint portions 66*gp* and 66*hp* and the yaw joint portions 66*gy* and 66*hy* of the manipulators 57*g* and 57*h*, respectively.

Advancing and retreating and rotational operation portions 104*gm* and 104*hm* are provided at the distal end sides of the tilting operation portions 104*gt* and 104*ht* through guide mechanisms 106*g* and 106*h*. In the guide mechanisms 106*g* and 106*h*, the guide axes of the advancing and retreating and rotational operation portions 104*gm* and 104*hm* are inserted into guide bores of the tilting operation portions 104*gt* and 104*ht*, and the advancing and retreating and rotational operation portions 104*gm* and 104*hm* are configured to advance and retreat in the axial directions of the tilting operation portions 104*gt* and 104*ht* and rotatable about roll axes R forming the central axes of the tilting operation portions 104*gt* and 104*ht*, relative to the tilting operation portions 104*gt* and 104*ht*. Electromagnetic brakes 55*gg* and 55*hg* are provided in the guide mechanisms 106*g* and 106*h*, and the electromagnetic brakes 55*gg* and 55*hg* are configured to be switched between releasing states to make the advancing and retreating and rotational operation portions 104*gm* and 104*hm* enable to advance and retreat, and rotate relative to the tilting operation portions 104*gt* and 104*ht*, and fixing states to make the advancing and retreating and rotational operation portions 104*gm* and 104*hm* unable to advance and retreat, and rotate relative to the tilting operation portions 104*gt* and 104*ht*. Moreover, advancing and retreating amount sensors 54*gm* and 54*hm* are provided in the guide mechanisms 106*g* and 106*h* and configured to detect amounts of advancing and retreating of the advancing and retreating and rotational operation portions 104*gm* and 104*hm* in the axial directions relative to the tilting operation portions 104*gt* and 104*ht*, and roll axial rotation angle sensors 54*gr* and 54*hr* are provided in the guide mechanisms 106*g* and 106*h* and configured to detect roll axial rotation angles of the advancing and retreating and rotational operation portions 104*gm* and 104*hm* about the roll axes R relative to the tilting operation portions 104*gt* and 104*ht*. The amounts of the advancing and retreating detected by the advancing and retreating amount sensors 54*gm* and 54*hm* are used for control of advancing and retreating actuations of the manipulators 57*g* and 57*h*, and the roll axial rotation angles detected by the roll axial rotation angle sensors 54*gr* and 54*hr* are used for control of rotational actuations of the manipulators 57*g* and 57*h* about the central axes.

In the manipulator masters 95g and 95h, opening and closing operation portions 104goc and 104hoc are provided on the distal end sides of the advancing and retreating and rotational operation portions 104gm and 104hm through pivot mechanisms 108g and 108h. The opening and closing operation portions 104goc and 104hoc are formed by pairs of opening and closing members configured to be opened and closed by the pivot mechanisms 108g and 108h, and the opening and closing directions of the pairs of opening and closing members substantially agree with the left and right direction of the first arm portion 96f of the endoscope master 95e in the normal arrangements. Electromagnetic brakes 55gp and 55hp are provided in the pivot mechanisms 108g and 108h, and the electromagnetic brakes 55gp and 55hp are configured to be switched between releasing states to make the opening and closing operation portions 104goc and 104hoc openable and closeable and fixing states to make the opening and closing operation portions 104goc and 104hoc unopenable and uncloseable. Moreover, opening and closing angle sensors 54goc and 54hoc are provided in the pivot mechanisms 108g and 108h and configured to detect opening and closeting angles of the pairs of opening and closing members. The opening and closing angles detected by the opening and closing angle sensors 54goc and 54hoc are used for control of opening and closing actuation of the grasping portion 64 of the grasping manipulator 57g and control of output of a high-frequency current to the high-frequency electrode 65 from the high-frequency power apparatus 92, respectively.

Furthermore, a leftward endoscope rotational operation button 111el and a rightward endoscope rotational operation button 111er are provided in tilting operation portions 104gt and 104ht on the left side and the right side, of the manipulator masters 95g and 95h, respectively. The leftward endoscope rotational operation button 111el and the rightward endoscope rotational operation button 111er are used for control of leftward rotational actuation and rightward rotational actuation of the endoscope 36 about the central axis, respectively.

Moreover, first link portion releasing buttons 112lf, second link portion releasing buttons 112ls and manipulator master releasing buttons 112 are provided at the tilting operation portions 104gt and 104ht of the manipulator masters 95g and 95h on the left side and the right side, respectively, and form releasing switch portions. All of the electromagnetic brakes 55lf, 55ls, 55gb, 55hb, 55gg, 55hg, 55gp and 55hp of the master apparatus 93 are normally in the fixing state, and the first and the second link portion 97f, 97s and the manipulator masters 95g and 95h are normally in the locking state. The first and the second link portion releasing buttons 112lf, 112ls are used to make the electromagnetic brake 55lf, 55ls of the first and the second link portion 97f, 97s in the releasing state to make the first and the second link portion 97f, 97s in the free state, respectively. The manipulator master releasing buttons 112 are used to make the electromagnetic brakes 55gb, 55hb, 55gg, 55hg, 55gp and 55hp of the manipulator masters 95g and 95h in the releasing state to make the manipulator masters 95g and 95h in the free states.

Referring to FIGS. 1 and 9 to 23, a method for using the medical system will be explained.

Here, in the medical system, operation signals and detected data are output to the system controller from the various buttons and various sensors, and actuation signals are output to the various electromagnetic brakes and the various motors from the system controller. However, the system controller is omitted for convenience of drawing in FIGS. 10, 11, 26 and 33.

Referring to FIG. 1, when the medical system is used, the endoscope 36 is inserted into the body such as the digestive organ and the abdominal cavity. The manipulator insertion portions 37g and 37h of the grasping manipulator 57g and the high-frequency treatment manipulator 57h are inserted into the grasping instrument channel 58g and the high-frequency treatment instrument channel 58h of the endoscope 36 and protrude from the grasping instrument protrusion opening 62g and the high-frequency treatment instrument protrusion opening 62h, respectively. An observation image around an object of treatment obtained by the endoscope 36 is displayed on the monitor 49. While the observation image displayed on the monitor 49 is observed, the master apparatus 93 is operated, and then, the endoscope 36 is actuated to move a field of view of the endoscope 36 appropriately, and the grasping treatment manipulator 57g and the high-frequency treatment manipulator 57h are actuated to perform treatment such as incision to an object of treatment. In this way, the endoscope 36, the grasping treatment manipulator 57g and the high-frequency treatment manipulator 57h are used together with one another.

Referring to FIGS. 9 and 10, when the master apparatus 93 is operated, the manipulator masters 95g and 95h on the left side and the right side are held by the left hand and the right hand, respectively. When the manipulator masters 95g and 95h are operated, the manipulator releasing buttons 112 of the manipulator masters 95g and 95h on the left side and the right side are turned on. Manipulator releasing operation signals are output to the system controller 48 from the manipulator releasing buttons 112 operated to be turned on. When the manipulator releasing operation signals are input to the system controller 48 from both the manipulator releasing buttons 112 on the left side and the right side, the system controller 48 outputs releasing actuation signals to the electromagnetic brakes 55gb, 55hb, 55gg, 55hg, 55gp and 55hp of the manipulator masters 95g and 95h to actuate the electromagnetic brakes 55gb, 55hb, 55gg, 55hg, 55gp and 55hp to be switched to the releasing states to make the manipulator masters 95g and 95h in the free states. Then, the manipulator masters 95g and 95h are operated with the manipulator releasing buttons 112 being turned on. On the other hand, when the first link portion 97f of the endoscope master 95e is operated, the first link portion releasing buttons 112lf in the manipulator masters 95g and 95h on the left side and the right side are turned on. First link portion releasing operation signals are output to the system controller 48 from the first link portion releasing buttons 112lf operated to be turned on. When the first link portion releasing operation signals are input to the system controller 48 from both the first link portion releasing buttons 112lf on the left side and the right side, the system controller 48 outputs a releasing actuation signal to the electromagnetic brake 55lf of the first link portion 97f to actuate the electromagnetic brake 55lf to be switched to the releasing state to make the first link portion 97f in the free state. Then, the manipulator masters 95g and 95h are held and moved with the first link portion releasing buttons 112lf being turned on, the first arm portion 96f is rotated through the support arms 103l and 103r, whereby the first link portion 97f is operated. Operation of the second link portion 97s is similar to that of the first link portion 97f.

Referring to FIGS. 9 and 10 and FIG. 1, when the leftward endoscope rotational operation button 111el or the rightward endoscope rotational operation button 111er of the manipulator masters 95g and 95h is turned on, a leftward rotational operation signal or a rightward rotational operation signal is output to the system controller 48 from the leftward endoscope rotational operation button 111el or the rightward endoscope rotational operation button 111er. The system controller 48 outputs a leftward rotational driving signal or a rightward rotational driving signal to the endoscope rotation driving motor 53*er* of the endoscope rotational driving portion 52*er* on the basis of the leftward rotational operation signal or the rightward rotational operation signal. The endoscope rotational driving motor 53*er* actuates the endoscope 36 to be rotated leftward or rightward about the central axis of the endoscope 36 on the basis of the leftward rotational driving signal or the rightward rotational driving signal. As a result, the distal end portions of the endoscope 36 and the manipulator apparatuses 63*g* and 63*h* are rotated about the central axis of the distal end portion of the endoscope 36 relative to an object of treatment. On the monitor 49, positions of the distal end portions of the manipulator apparatuses 63*g* and 63*h* are not changed and an object of observation is rotated.

Referring to FIGS. 9 and 10 and FIGS. 12 and 13, when the first and the second link portion 97*f*, 97*s* of the endoscope master 95*e* is operated to be rotated, rotation angles in the up and down direction and the left and right direction of the first and the second link portion 97*f*, 97*s* are detected by the first and the second up and down directional, and left and right directional rotation angle sensor 54*fu*, 54*fl*, 54*su*, 54*sl*, respectively. The rotation angle sensors 54*fu*, 54*fl*, 54*su* and 54*sl* output data for the rotation angles to the system controller 48. The system controller 48 outputs bending actuation signals to the first and the second up and down directional, and left and right directional endoscope bending driving motors 53*efu*, 53*efl*, 53*esu*, 53*esl* of the endoscope bending driving portion 52*eb* on the basis of the input data for the rotation angle, and the endoscope bending driving motors 53*efu*, 53*efl*, 53*esu*, 53*esl* actuate the first and the second endoscope bending portion 51*ef*, 51*es* to be bent on the basis of the input bending actuation signal, respectively. The system controller 48 controls the first and the second up and down direction, and left and right directional endoscope bending driving motor 53*efu*, 53*efl*, 53*esu*, 53*esl* such that the rotation angle detected by the first and the second up and down directional, and left and right directional rotation angle sensor 54*fu*, 54*fl*, 54*su*, 54*sl* is substantially equal to the bending angle in the up and down direction and the left and right direction of the first and the second endoscope bending portion 51*ef*, 51*es*, respectively. As a result, the distal end of the endoscope 36 is moved, and therefore, a field of view of observation of the endoscope 36 is moved. On the monitor 49, positions of the distal end portions of the manipulator apparatus 63*g* and 63*h* are not changed and an object of observation is moved. The rotation angle of the first and the second link portion 97*f*, 97*s* in the endoscope master 95*e* substantially agrees with the bending angle of the first and the second endoscope bending portion 51*ef*, 51*es* in the endoscope 36. Then, the whole shape of the endoscope master 95*e* corresponds to the whole shape of the distal end portion of the endoscope 36. Then, the whole shape of the distal end portion of the endoscope 36, which it is difficult to visually confirm, can be understood on the basis of the whole shape of the endoscope master 95*e*.

Referring to FIGS. 9 and 11 and FIGS. 14 and 15, when the tilting operation portion 104*gt* or 104*ht* of the manipulator master 95*g* or 95*h* is operated to be rotated about the pitch axis P, the pitch axial rotation angle is detected by the pitch axial rotation angle sensor 54*gp* or 54*hp* of the ball joint 105*g* or 105*h*. The pitch axial rotation angle sensor 54*gp* or 54*hp* outputs data for the pitch axial rotation angle to the system controller 48. The system controller 48 outputs pitch axial rotational driving signal to the pitch axial rotational driving motor 53*gp* or 53*hp* of the manipulator driving unit 39*g* or 39*h* on the basis of the input data for the pitch axial rotation angle, the pitch axial rotational driving motor 53*gp* or 53*hp* actuates the pitch joint portion 66*gp* or 66*hp* of the manipulator 57*g* or 57*h* to be rotated to move the grasping portion 64 or the high-frequency electrode 65 in the pitch direction on the basis of the input pitch axial rotational driving signal. The system controller 48 controls the pitch axial rotational driving motor 53*gp* or 53*hp* such that the pitch axial rotation angle detected by the pitch axial rotation angle sensor 54*gp* or 54*hp* is substantially equal to rotation angle of the pitch joint portion 66*gp* or 66*hp*.

Referring to FIGS. 9 and 11 and FIGS. 16 and 17, when the tilting operation portion 104*gt* or 104*ht* is operated to be rotated about the yaw axis Y relative to the terminal end portion of the support arm 103*l* or 103*r* in the manipulator master 95*g* or 95*h*, the yaw joint portion 66*gy* or 66*hy* is actuated to be rotated such that the yaw axial rotation angle detected by the yaw axial rotation angle sensor 54*gy* or 54*hy* is substantially equal to the rotation angle of the yaw joint portion 66*gy* or 66*hy*, and the grasping portion 64 or the high-frequency electrode 65 is moved in the yaw direction, similarly to the case for the pitch axis P.

Referring to FIGS. 9 and 11 and FIGS. 18 and 19, when the advancing and retreating and rotational operation portion 104*gm* or 104*hm* is operated to be advanced and retreated in the axial direction relative to the tilting operation portion 104*gt* or 104*ht* of the manipulator master 95*g* or 95*h*, an amount of advancing and retreating is detected by the advancing and retreating amount sensor 54*gm* or 54*hm* of the guide mechanism 106*g* or 106*h*. The advancing and retreating amount sensor 54*gm* or 54*hm* outputs data for the amount of the advancing and retreating to the system controller 48. The system controller 48 outputs an advancing and retreating actuation signal to the advancing and retreating driving motor 53*gm* or 53*hm* of the manipulator driving unit 39*g* or 39*h* on the basis of the input data for the amount of the advancing and retreating, the advancing and retreating driving motor 53*gm* or 53*hm* actuates the whole manipulator 57*g* or 57*h* to be advanced and retreated on the basis of the input advancing and retreating actuation signal to actuate the grasping portion 64 or the high-frequency electrode 65 of the distal end of the manipulator 57*g* or 57*h* to be advanced and retreated. The system controller 48 controls the advancing and retreating driving motor 53*gm* or 53*hm* such that a ratio of an amount of advancing and retreating of the whole manipulator 57*g* or 57*h* to the amount of the advancing and retreating detected by the advancing and retreating amount sensor 54*gm* or 54*hm* is substantially fixed.

Referring to FIGS. 9 and 11 and FIGS. 20 and 21, when the advancing and retreating and rotational operation portion 104*gm* or 104*hm* is operated to be rotated about the roll axis R relative to the tilting operation portion 104*gt* or 104*ht* in the manipulator master 95*g* or 95*h*, the roll axial rotation angle is detected by the roll axial rotation angle sensor 54*gr* or 54*hr* of the guide mechanism 106*g* or 106*h*. The roll axial rotation angle sensor 54*gr* or 54*hr* outputs data for the roll axial rotation angle to the system controller 48. The system controller 48 outputs a rotational driving signal to the manipulator rotational driving motor 53*gr* or 53*hr* of the manipulator driving unit 39*g* or 39*h* on the basis of the input data for the roll axial rotation angle, the manipulator rotational driving motor 53*gr* or 53*hr* actuates the whole manipulator 57*g* or 57*h* to be rotated about the central axes of the manipulator 57*g* or 57*h* on the basis of the input rotational driving signal, and the grasping portion 64 or the high-frequency electrode 65 of the distal end of the manipulator 57*g* or 57*h* is actuated to be moved in the roll direction. The system controller 48 controls the manipulator rotational driving motor 53*gr* or 53*hr* such that the roll axial rotation angle detected by the roll axial rotation angle sensor 54gr or 54hr is substantially equal to the rotation angle of the whole manipulator 57g or 57h about the central axis of the manipulator 57g or 57h.

Referring to FIGS. 9 and 11 and FIGS. 22 and 23, when the opening and closing operation portion 104goc or 104hoc is operated to be opened and closed in the manipulator master 95g or 95h, an opening and closing angle is detected by the opening and closing angle sensor 54goc or 54hoc of the pivot mechanism 108g or 108h. The opening and closing angle sensors 54goc and 54hoc output data for the opening and closing angles to the system controller 48. Regarding the grasping manipulator master 95g and the grasping manipulator apparatus 63g, the system controller 48 outputs opening and closing actuation signal to the opening and closing driving motor 53oc of the manipulator driving unit 39g on the basis of the input data for the opening and closing angle, and the opening and closing driving motor 53oc actuates the grasping portion 64 to be opened and closed on the basis of the input opening and closing actuation signal. The system controller 48 controls the opening and closing driving motor 53oc such that the opening and closing angle detected by the opening and closing angle sensor 54goc is substantially equal to an opening and closing angle of the grasping portion 64. On the other hand, regarding the high-frequency treatment manipulator master 95h and the high-frequency treatment manipulator apparatus 63h, the system controller 48 outputs an output signal to the high-frequency power apparatus 92 when the opening and closing angle detected by the opening and closing angle sensor 54hoc is smaller than a threshold, and the high-frequency power apparatus 92 outputs a high-frequency current to the high-frequency electrode 65 on the basis of the output signal.

In the above mentioned operation of the master apparatus 93 and actuations of the endoscope 36 and the manipulator apparatuses 63g and 63h, the relative arrangement between the endoscope master 95e, the grasping manipulator master 95g and the high-frequency treatment manipulator master 95h in the master apparatus 93 corresponds to the relative arrangement between the distal end rigid portion 38 as a portion to be actuated in the endoscope 36, the grasping manipulator 57g as a portion to be actuated in the grasping portion 64 and the high-frequency electrode 65 as a portion to be actuated in the high-frequency treatment manipulator 57h. That is, in the present embodiment, the grasping manipulator master 95g and the high-frequency treatment manipulator master 95h are arranged on the left side and the right side relative to the central axis of the first arm portion 96f of the endoscope master 95e, respectively. According to this, the distal end portions of the grasping manipulator 57g and the high-frequency treatment manipulator 57h are arranged on the left side and the right side relative to the central axis of the distal end rigid portion 38 of the endoscope 36, respectively. Furthermore, attitudes of the grasping manipulator master 95g and the high-frequency treatment manipulator master 95h relative to the first arm portion 96f substantially agree with attitudes of the grasping portion 64 of the grasping manipulator 57g and the high-frequency electrode 65 of the high-frequency treatment manipulator 57h relative to the distal end rigid portion 38, respectively. In detail, angles formed by the central axes of the manipulator masters 95g and 95h relative to the up and down direction, the left and right direction and the axial direction of the first arm portion 96f substantially agree with angles formed by the central axes of the grasping portion 64 and the high-frequency electrode 65 relative to the up and down direction, the left and right direction and the axial direction of the distal end rigid portion 38, respectively. Moreover, angles formed by the opening and closing direction of the grasping manipulator master 95g relative to the up and down direction, the left and right direction and the axial direction of the first arm portion 96f substantially agree with angles formed by the opening and closing direction of the grasping portion 64 relative to the up and down direction, the left and right direction and the axial direction of the distal end rigid portion 38, respectively. In this way, the relative arrangements substantially agree with each other, and therefore, positional relationships can be easily understood in the medical system.

The medical system according to the present embodiment has the following effects.

In the medical system according to the present embodiment, the endoscope 36 performs following actuation by operation input to the endoscope master 95e, and the manipulators 57g and 57h perform following actuations by operation inputs to the manipulator masters 95g and 95h. Then, the endoscope master 95e can be operated through the support arms 103l and 103r by holding and operating the manipulator masters 95g and 95h, and therefore, the endoscope 36 and the manipulators 57g and 57h can perform the following actuations solely by operating the manipulator masters 95g and 95h. Moreover, the relative arrangement between the endoscope master 95e, the grasping manipulator master 95g and the high-frequency treatment manipulator master 95h corresponds to the relative arrangement between the distal end rigid portion 38 of the endoscope 36, the grasping portion 64 of the grasping manipulator 57g and the high-frequency electrode 65 of the high-frequency treatment manipulator 57h, and therefore, the positional relationship can be easily understood in the medical system. Furthermore, when the first and the second link portion 97f, 97s is made in the locking state, the grasping and the high-frequency treatment manipulator master 95g, 95h is made in the free state and the grasping manipulator master 95g and the high-frequency treatment manipulator master 95h is operated, the grasping and the high-frequency treatment manipulator master 95g, 95h can be stably and smoothly operated. Moreover, when the first and the second link portion 97f, 97s is made in the free state, the grasping and the high-frequency treatment manipulator master 95g, 95h is made in the locking state and the first and the second link portion 97f, 97s is operated by the grasping and the high-frequency treatment manipulator master 95g, 95h through the support arm 103l, 103r, the first and the second link portion 97f, 97s can be stably and smoothly operated. Therefore, the operability of the medical system is sufficiently improved.

Figure 24:
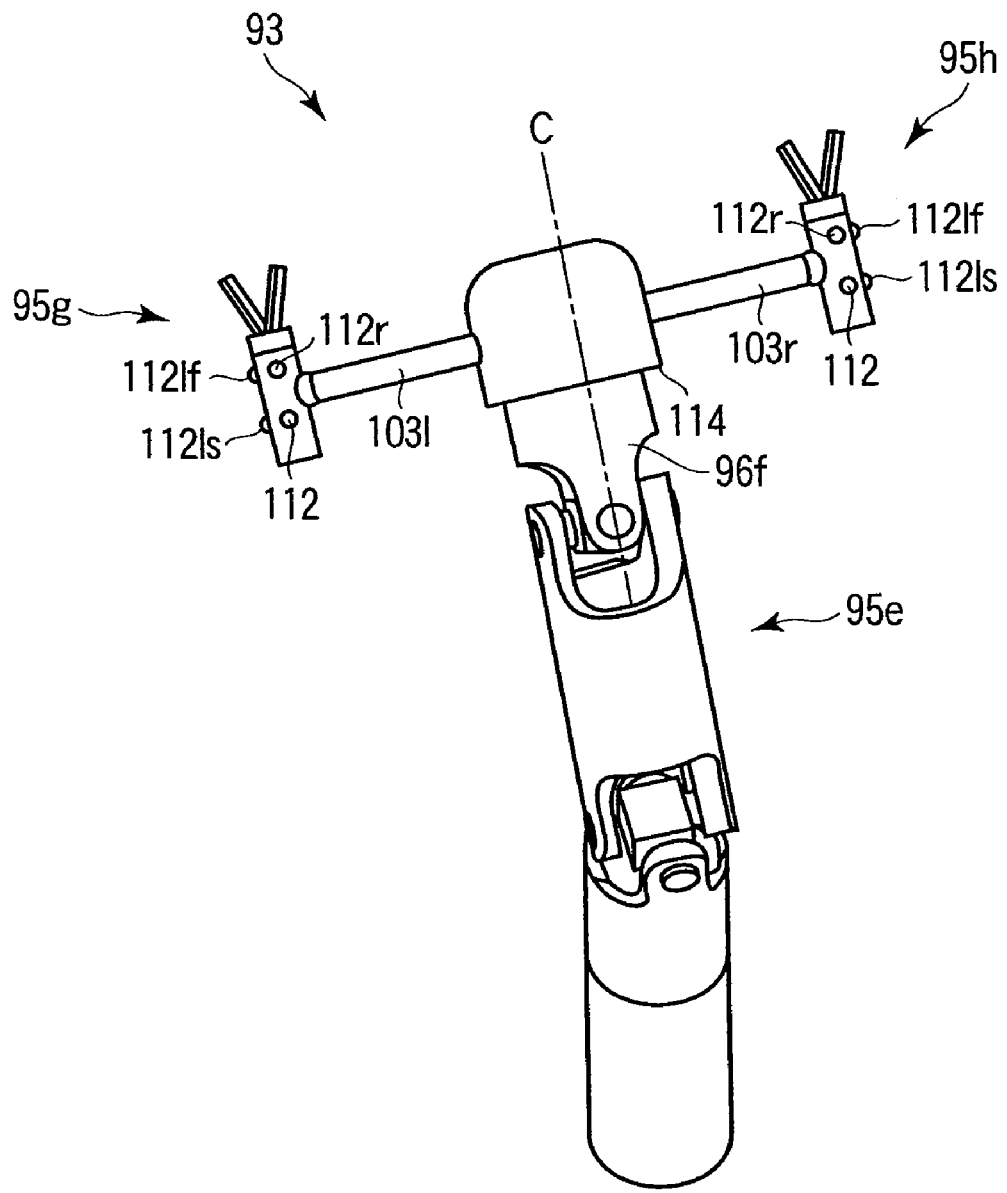
FIG. 24 is a perspective view showing a master apparatus according to a second embodiment of the present invention.
Figure 25:
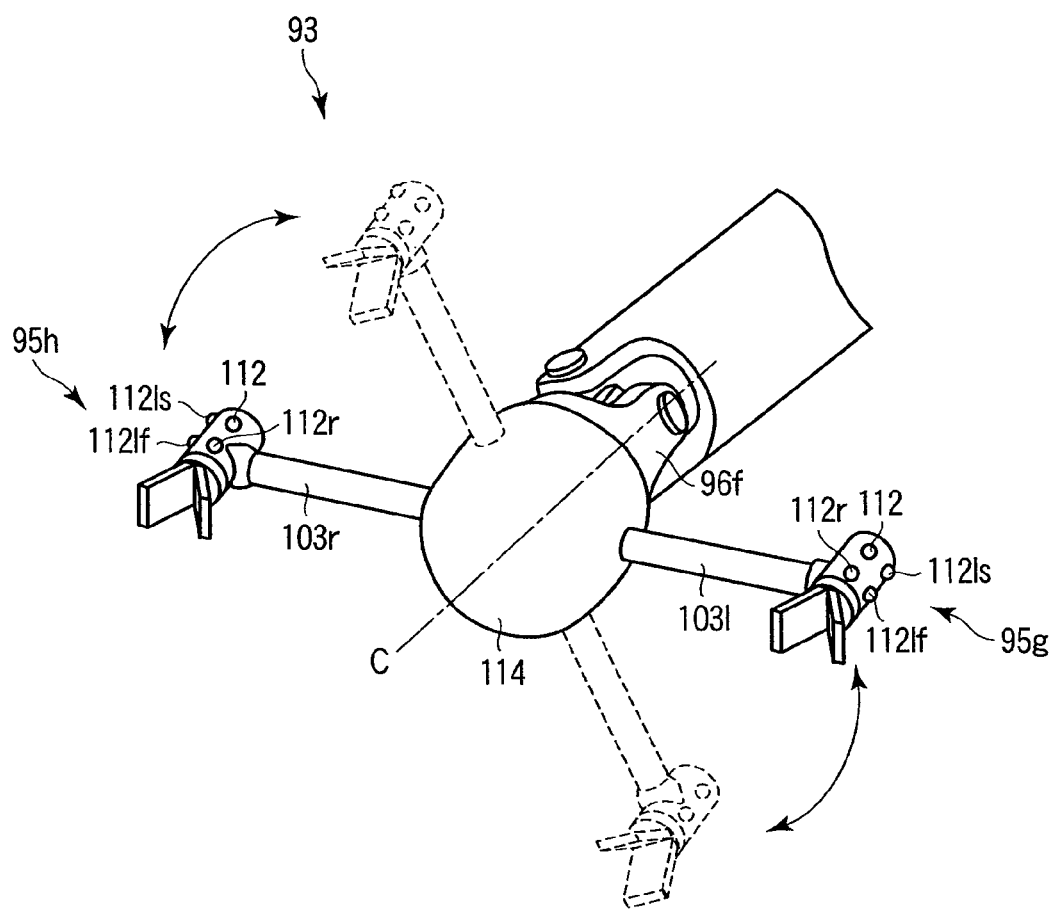
FIG. 25 is a perspective view showing rotational operation of a distal end rotational portion of an endoscope master according to the second embodiment of the present invention.
Figure 26:
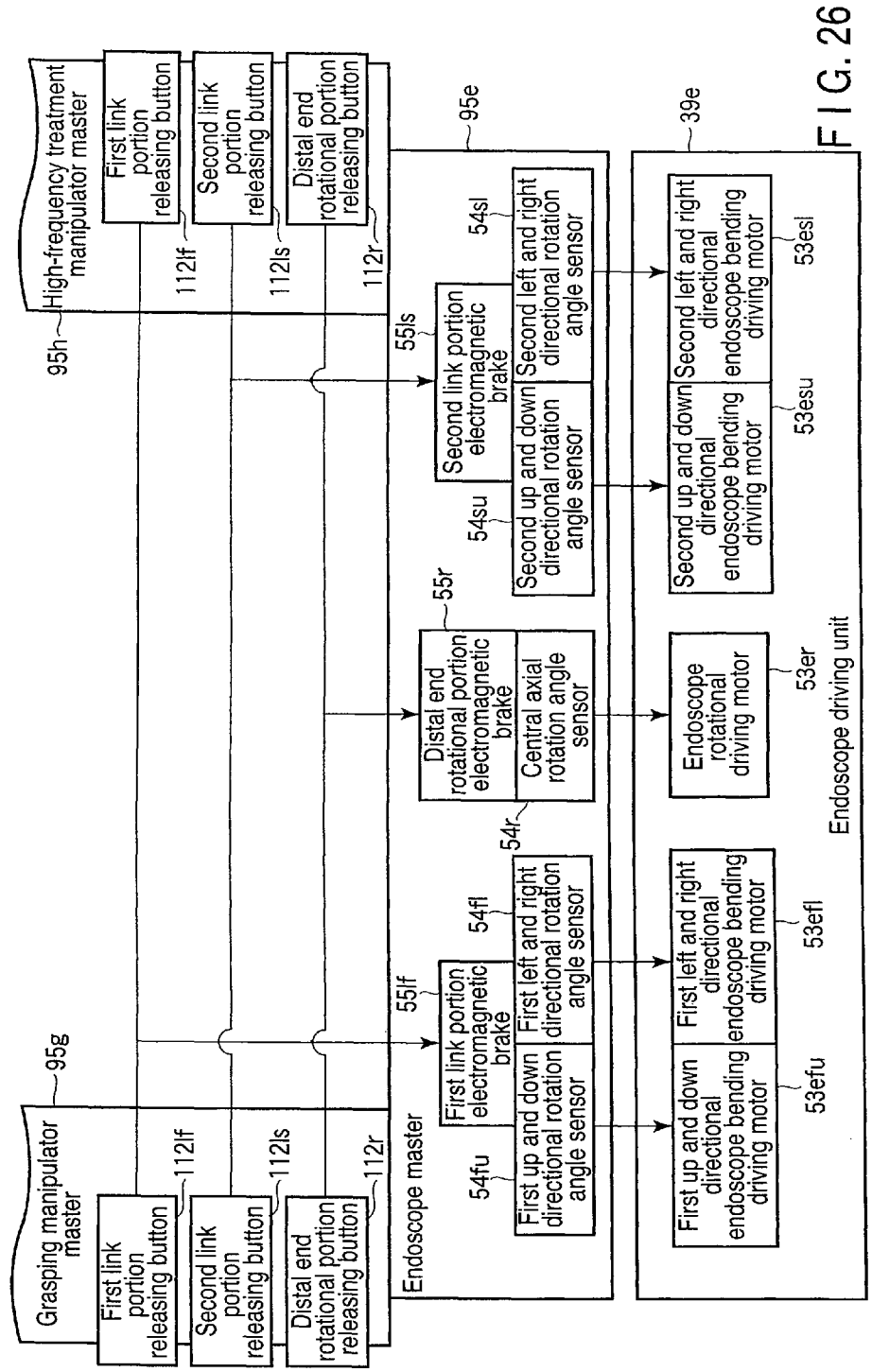
FIG. 26 is a block diagram showing a control system of an endoscope apparatus in a medical system according to the second embodiment of the present invention.

Referring to FIGS. 24 to 26, a second embodiment of the present invention will be explained.

Referring to FIGS. 24 and 25, in a master apparatus 93 according to the present embodiment, a distal end rotational portion 114 is provided on the distal end side of a first arm portion 96f in an endoscope master 95e. The distal end rotational portion 114 is rotatable about the central axis C of the first arm portion 96f relative to the first arm portion 96f. An electromagnetic brake 55r is interposed between the first arm portion 96f and the distal end rotational portion 114, and the electromagnetic brake 55r is configured to be switched between a releasing state to make the distal end rotational portion 114 rotatable relative to the first arm portion 96f and a fixing state to make the distal end rotational portion 114 unrotatable relative to the first arm portion 96f. Moreover, a central axial rotation angle sensor 54r is provided between the first arm portion 96f and the distal end rotational portion 114 and configured to detect a rotation angle of the distal end rotational portion 114 relative to the first arm portion 96f. The root portions of support arms 103*l* and 103*r* on the left side and the right side are coupled to both end portions of the distal end rotational portion 114 which is the left end portion and the right end portion in the normal position, respectively. The distal end rotational portion releasing buttons 112*r* are used in manipulator masters 95*g* and 95*h* coupled to the terminal end portions of the support arms 103*l* and 103*r* instead of the endoscope rotational operation buttons 111*el* and 111*er*.

Referring to FIGS. 25 and 26, when the distal end rotational portion 114 is operated to be rotated, the distal end rotational portion releasing buttons 112*r* of the manipulator masters 95*g* and 95*h* on the left side and the right side are turned on. Distal end rotational portion releasing operation signals are output to the system controller 48 from the distal end rotational portion releasing buttons 112*r* turned on. When the distal end rotational portion releasing operation signals are input to the system controller 48 from both the distal end rotational portion releasing buttons 112*r* on the left side and the right side, the system controller 48 outputs a release signal to the electromagnetic brake 55*r* between the first arm portion 96*f* and the distal end rotational portion 114, and the electromagnetic brake 55*r* is actuated to be switched to the releasing state to make the distal end rotational portion 114 in the free state. When the manipulator masters 95*g* and 95*h* are held and moved to be rotated about the central axis C of the first arm portion 96*f* with the distal end rotational portion releasing button 112*r* being turned on, the distal end rotational portion 114 is operated to be rotated about the central axis C of the first arm portion 96*f* relative to the first arm portion 96*fr*. The central axial rotation angle sensor 54*r* detects a rotation angle of the distal end rotational portion 114 relative to the first arm portion 96*f* and outputs data for the rotation angle to the system controller 48. The system controller 48 outputs a rotation driving signal to the endoscope rotational driving motor 53*e* of the endoscope rotational driving portion 52*er* on the basis of the input data for the rotation angle. The endoscope rotational driving motor 53*er* actuates the endoscope 36 to be rotated about the central axis of the endoscope 36 on the basis of the input rotational driving signal. The system controller 48 controls the endoscope rotational driving motor 53*er* such that the central axial rotation angle detected by the central axial rotation angle sensor 54*r* is substantially equal to a rotation angle of the endoscope 36.

In the medical system according to the present embodiment, when the manipulator masters 95*g* and 95*h* are rotationally moved about the central axis C of the first arm portion 96*f* relative to the first arm portion 96*f* and the distal end rotational portion 114 is operated to be rotated about the central axis C of the first arm portion 96*f* relative to the first arm portion 96*f*, the endoscope 36 is actuated to be rotated about the central axis of the endoscope 36 at a rotation angle substantially equal to the rotation angle of the distal end rotational portion 114. Therefore, the rotational actuation of the endoscope 36 can be intuitively and precisely operated.

Here, in the present embodiment, although the rotation angle sensor is used for detecting a rotation angle, a medical system may be formed with a rotation direction sensor configured to detect a rotation direction instead of a rotation angle sensor.

Figure 27:
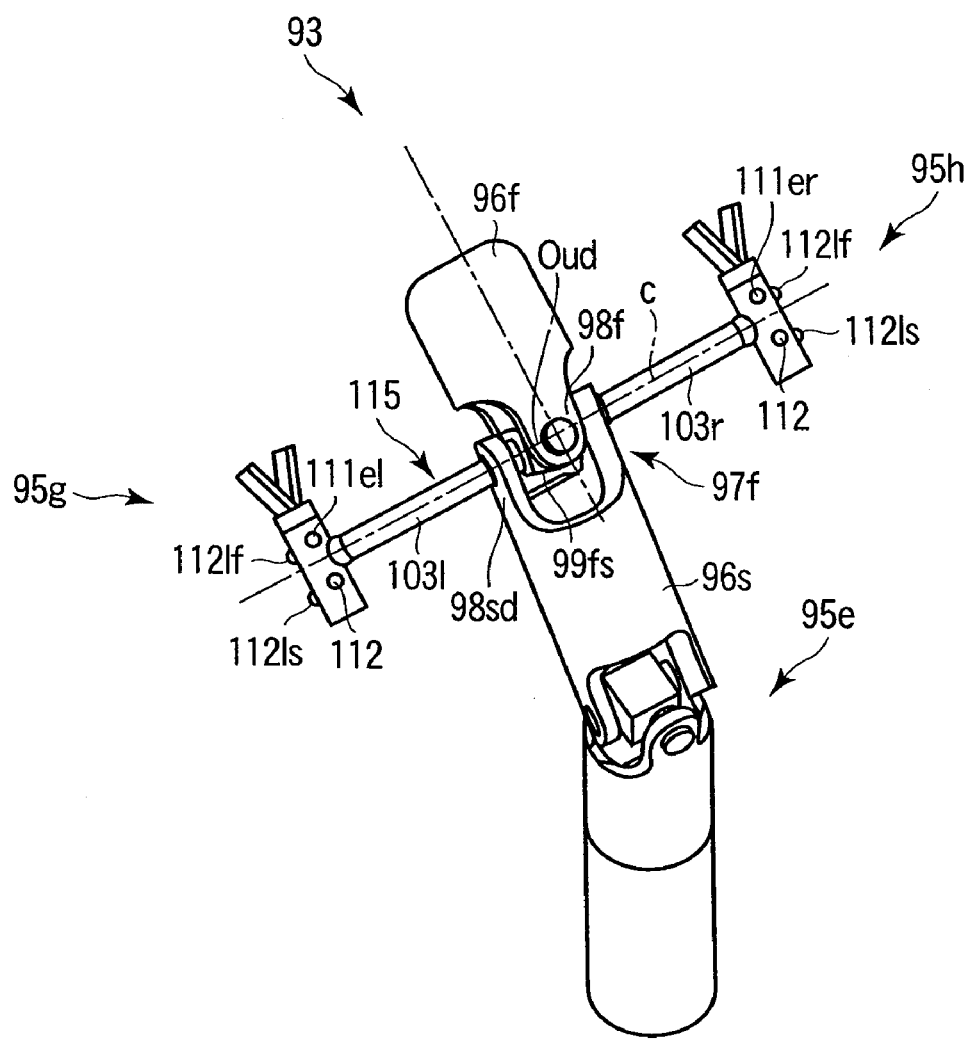
FIG. 27 is a perspective view showing a master apparatus according to a third embodiment the present invention.
Figure 28:
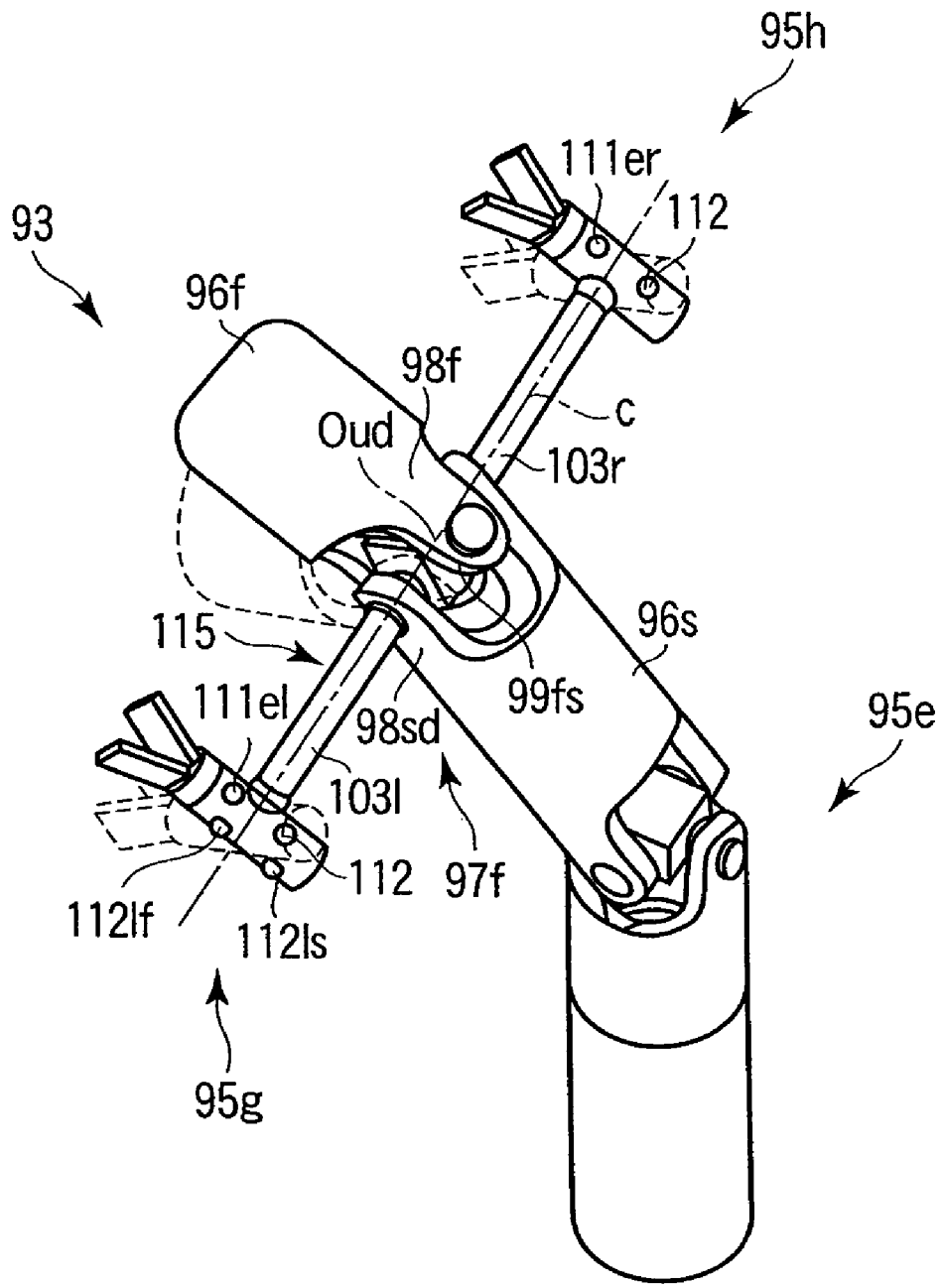
FIG. 28 is a perspective view showing rotational operation in the up and down direction of a first link portion of an endoscope master according to the third embodiment of the present invention.

Referring to FIGS. 27 and 28, a third embodiment of the present invention will be explained.

In a master apparatus 93 according to the present embodiment, a rod-like support member 115 extends along an up and down directional rotation axis Oud of a first arm portion 96*f* and passes through a first link portion 97*f*. The parts on left end side and right end side of the support member 115 form support arms 103*l* and 103*r* on the left side and the right side, respectively. In the first link portion 97*f*, the support member 115 extends and penetrates a pair of tongue portions 98*sd* of the distal end portion of a second arm portion 96*s* and the support member 115 is supported by the pair of tongue portions 98*sd* so as to be rotatable about the central axis C of the support member 115 relative to the pair of tongue portions 98*sd*. In the present embodiment, the terminal end portions of the support arms 103*l* and 103*r* as connecting portions form connecting portion rotational end portions, and the central portions of the support arms 103*l* and 103*r* form connecting portion support portions. Moreover, the support member 115 extends and penetrates a rotational block 99*fs* and is fixed to the rotational block 99*fs*. Tongue portions 98*f* of the proximal end portion of the first arm portion 96*f* are fixed to the rotational block 99*fs*. In the present embodiment, the tongue portions 98*f* of the proximal end portion of the first arm portion 96*f* as a movement portion form a movement portion support portion, and the distal end portion of the first arm portion 96*f* forms a movement portion rotational end portion.

When first link portion releasing buttons 112*lf* of the manipulator masters 95*g* and 95*h* are turned on and the manipulator masters 95*g* and 95*h* are operated to be rotated about the central axis C of the support member 115, the support member 115, the rotational block 99*fs* and the first arm portion 96*f* are operated to be rotated integrally about the central axis C of the support member 115 and the first arm portion 96*f* is operated to be rotated in the up and down direction.

Here, in the case where the central axis C of the support member 115 is arranged at the distal end portion of the first arm portion 96*f*, it is necessary to operate the manipulator masters 95*g* and 95*h* to a large extent to be rotated about the up and down directional rotation axis Oud of the first arm portion 96*f* in order to operate the first arm portion 96*f* to be rotated in the up and down direction, and a movement range in which the manipulator masters 95*g* and 95*h* are moved becomes comparatively large. In contrast, in the medical system according to the present embodiment, the central axis C of the support member 115 agrees with the up and down directional rotation axis Oud of the first arm portion 96*f*. Therefore, the first arm portion 96*f* can be operated to be rotated in the up and down direction merely by operating the manipulator masters 95*g* and 95*h* to a small extent to be rotated about the central axis C of the support member 115, and then, the movement range in which the manipulator masters 95*g* and 95*h* are moved becomes comparatively small. Therefore, the operability of the medical system is further improved.

Here, although a manipulator is inserted through an instrument channel of an endoscope in the above mentioned embodiments, the manipulator may be inserted through a channel tube attached to the outside of the endoscope.

Referring to FIGS. 29 to 33, a fourth embodiment of the present invention will be explained.

Figure 29:
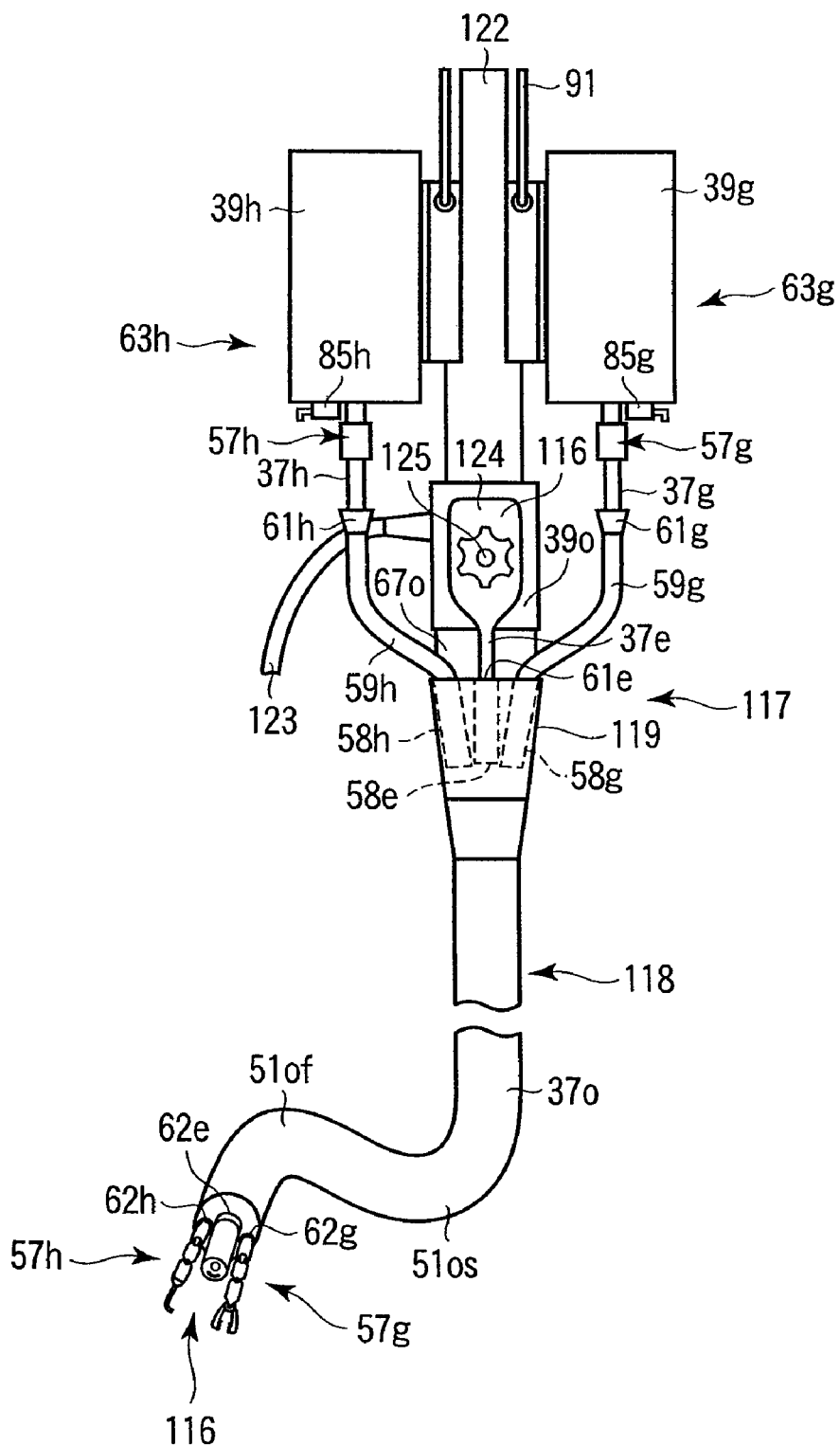
FIG. 29 is a perspective view showing an endoscope, a manipulator apparatus and an overtube apparatus according to a fourth embodiment of the present invention.

Referring to FIGS. 29 and 30, in a medical system according to the present embodiment, an overtube apparatus 117 is used as an insertion slave apparatus. The overtube apparatus 117 is formed by an overtube 118 and an overtube driving unit 39*o*. Moreover, instead of the electrical bending endoscope 36, a manually bending endoscope 116 is used. Here, a bending portion is provided in the distal end portion of an insertion portion 37*e* of the endoscope 116 and configured to be actuated to be bent in an up and down direction. An operation portion 124 is coupled to the proximal end portion of the insertion portion 37*e* and configured to be held and operated by an operator. A bending operation knob 125 is provided in the operation portion 124 and configured to operate the bending portion to be bent. Furthermore, a grasping manipulator apparatus 63g and a high-frequency treatment manipulator apparatus 63h are used, which are similar to those according to the first embodiment, respectively. Here, manipulator driving units 39g and 39h of the manipulator apparatuses 63g and 63h are held by a stand 122 of a trolley 41.

Figure 31:
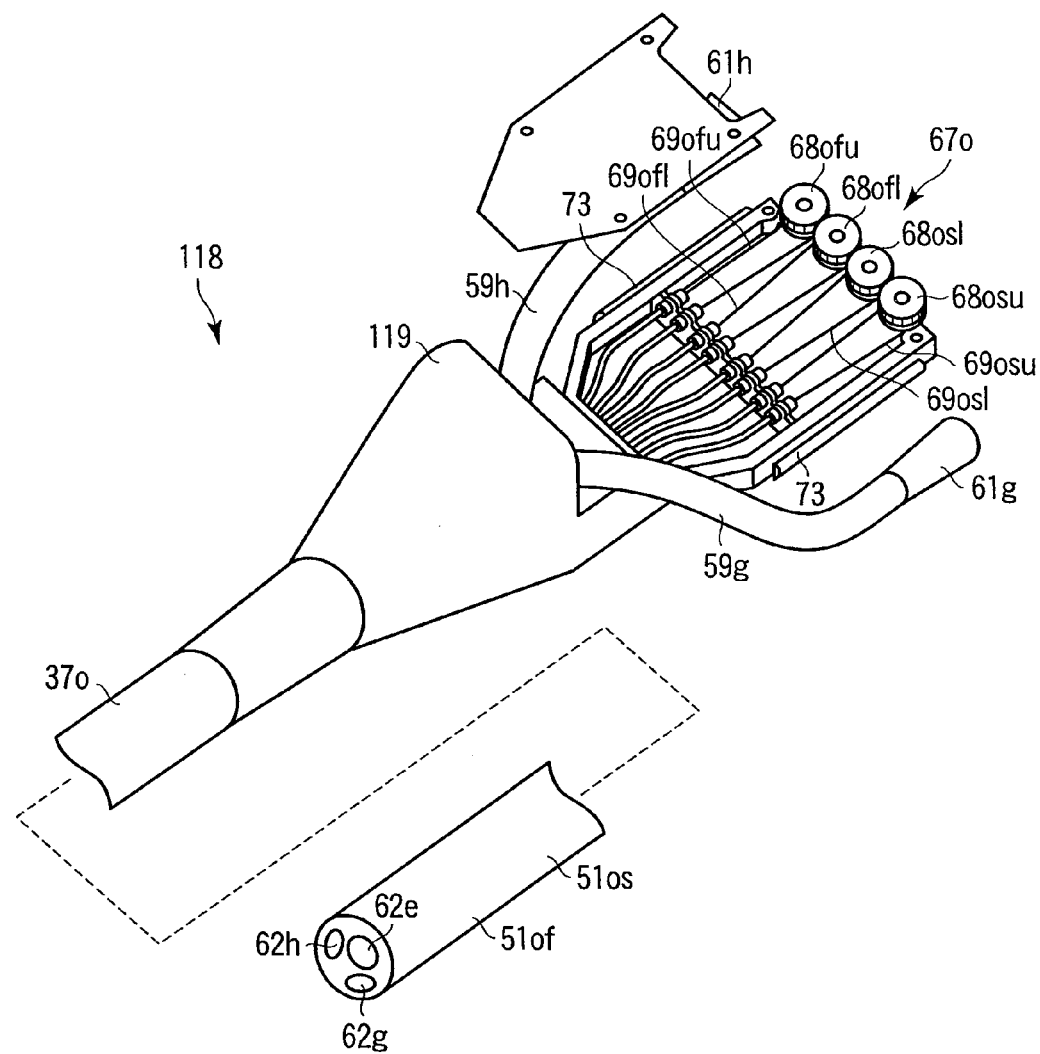
FIG. 31 is an exploded perspective view showing an overtube according to the fourth embodiment of the present invention.

Referring to FIGS. 29, 30 and 31, the overtube 118 includes an overtube insertion portion 37o being long and flexible and configured to be inserted into the body. A first overtube bending portion 51of and a second overtube bending portion 51os are arranged in the axial direction in the distal end portion of the overtube insertion portion 37o and configured to be actuated to be bent in an up and down direction and a left and right direction. An overtube connecting portion 119 is coupled to the proximal end portion of the overtube insertion portion 37o. An endoscope channel 58e, a grasping instrument channel 58g and a high-frequency treatment instrument channel 58h extend in the overtube insertion portion 37o and the overtube connecting portion 119, and the endoscope 116, the grasping treatment manipulator 57g and the high-frequency treatment manipulator 57h are configured to be inserted through the endoscope channel 58e, the grasping instrument channel 58g and the high-frequency treatment instrument channel 58h, respectively. The distal end portions of the endoscope channel 58e, the grasping treatment instrument channel 58h and the high-frequency treatment instrument channel 58h are connected to an endoscope protrusion opening 62e, a grasping instrument protrusion opening 62g and a high-frequency treatment instrument protrusion opening 62h formed in the distal end portion of the overtube insertion portion 37o. On the other hand, the proximal end portion of the endoscope channel 58e is connected to an endoscope insertion opening 61e formed in the overtube connecting portion 119. Moreover, the proximal end portions of the grasping instrument channel 58g and the high-frequency treatment instrument channel 58h are connected to a grasping instrument guide pipe 59g and a high-frequency treatment instrument guide pipe 59h in the overtube connecting portion 119, similarly to the first embodiment.

A cassette-like overtube actuation connecting portion 67o is provided at the proximal end portion of the overtube connecting portion 119. In the overtube actuation connecting portion 67o, a first up and down directional bending pulley 68ofu and a first up and down directional overtube wire 69ofu for actuating the first overtube bending portion 51of to be bent in the up and down direction, a first left and right directional bending pulley 68ofl and a first left and right directional overtube wire 69ofl for actuating the first overtube bending portion 51of to be bent in the left and right direction, a second up and down directional bending pulley 68osu and a second up and down directional overtube wire 69osu for actuating the second overtube bending portion 51os to be bent in the up and down direction and a second left and right directional bending pulley 68osl and a second left and right directional overtube wire 69osl for actuating the second overtube bending portion 51os to be bent in the left and right direction are used. The one end side parts and the other end side parts of the overtube wires 69ofu, 69ofl, 69osu and 69osl are inserted through the overtube connecting portion 119 and the overtube insertion portion 37o and coupled to the overtube bending portions 51of and 51os. When the bending pulley 68ofu, 68ofl, 68osu or 68osl is actuated to be rotated and the overtube wire 69ofu, 69ofl, 69osu or 69osl is actuated to be advanced and retreated, the overtube bending portion 51of or 51os is actuated to be bent. Moreover, a guide convex portion 73 and a click hole 74 are formed in the overtube actuation connecting portion 67o, similarly to the manipulator driving connecting portions 67g and 67h (referring to FIGS. 3 and 4).

Referring to FIGS. 29, 30, 32 and 33, an overtube connecting portion housing 82o and an overtube connecting portion engaging portion 85o are provided in a main portion 121 of the overtube driving unit 390 and have similar configurations to those of the manipulator connecting portion housing portions 82g and 82h and the manipulator connecting portion engaging portions 85g and 85h of the manipulator driving units 39g and 39h according to the first embodiment (referring to FIGS. 6 to 8). A first and a second up and down directional, and left and right directional overtube bending driving portion are provided within the main portion 121 and have similar configurations to those of the actuation portion 52gp, 52hp, 52gv, 52hy, 52oc within the manipulator rotational portion 79g or 79h according to the first embodiment (referring to FIGS. 6 to 8). The first and the second up and down directional, and right and left overtube bending driving portion includes a first and a second up and down directional, and left and right directional overtube bending driving motor 53ofu, 53ofl, 53osu, 53osl. The overtube driving unit 390 is held by the stand 122 of the trolley 41 and connected to the system controller through the overtube cord 123. Moreover, the operation portion 117 of the endoscope 116 is configured to be attached to and detached from the main portion 121 of the overtube driving unit 390 by an attachment and detachment mechanism which is not shown.

Referring to FIG. 33, a master apparatus used in the present embodiment is similar to the master apparatus 93 according to the first embodiment as is shown in FIG. 9. However, the endoscope master 95e is used as an overtube master 95o for operating the overtube 118 and the endoscope rotational operation buttons 111el and 111er are not used. When a first link portion 97f of the overtube master 95o is operated to be rotated, rotation angles in the up and down direction and left and right direction in the first link portion 97f are detected by a first up and down directional rotation angle sensor 54fu and a first left and right rotation angle sensor 54fl, respectively. Similarly, rotation angles in the up and down direction and the left and right direction in a second link portion 97s are detected by a second up and down directional rotation angle sensor 54su and a second left and right directional rotation angle sensor 54sl. The rotation angle sensors 54fu, 54fl, 54su and 54sl output data for the rotation angles to the system controller 48. The system controller 48 outputs bending actuation signals to the first and the second up and down directional, and left and right directional overtube bending driving motors 53ofu, 53ofl, 53osu, 53osl of the overtube driving unit 390 on the basis of the input data for the rotation angle, and the overtube bending driving motors 53ofu, 53ofl, 53osu, 53osl actuate the first and the second overtube bending portion 51of, 51os to be bent on the basis of the input bending actuation signals. The system controller 48 controls the first and the second up and down directional, and the left and right directional overtube bending driving motors 53ofu, 53ofl, 53osu, 53osl such that the rotation angle detected by the first and the second up and down directional, and left and right directional rotation angle sensors 54fu, 54fl, 54su, 54sl are substantially equal to bending angle of the first and the second overtube bending portion 51of, 51os in the up and down direction and the left and right direction.

In the medical system according to the present embodiment, the operability of the medical system is sufficiently improved similarly to the medical system according to the first embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical system comprising:
    an insertion slave apparatus configured to be inserted into a body and including an insertion portion;
    a treatment slave apparatus comprising a manipulator and a manipulator driving unit, the manipulator being configured to be inserted into the body through a channel extending through the insertion portion of the insertion slave apparatus, the treatment slave apparatus configured to be used together with the insertion slave apparatus to treat an object of treatment;
    an insertion master portion including a movable portion, and a movable support portion, the movable portion including a movement portion rotational end portion formed in one end portion of the movable portion, and a movement portion support portion formed in an other end portion of the movable portion and supported by the movable support portion such that the movement portion rotational end portion is configured to rotate in a rotational direction about the movement portion support portion as a center of rotation;
    a treatment master portion configured to be operated by an operator, wherein the treatment slave apparatus is configured to perform following actuation according to operation input to the treatment master portion; and
    a support arm connecting portion coupling the insertion master portion and the treatment master portion to each other, wherein the insertion master portion is configured to be operated through the support arm connecting portion by holding and operating the treatment master portion wherein the support arm connecting portion includes a connection portion rotational end portion formed in one end portion of the support arm connecting portion and coupled to the treatment master portion, and a connecting portion support portion formed in the outer end portion of the support arm connecting portion and supported by the movable support portion such that the connecting portion rotational end portion is configured to rotate in the rotational direction about the center of rotation,
    wherein a first bending portion and a second bending portion are arranged in the axial direction in the distal end portion of the insertion portion of the insertion slave apparatus and configured to be actuated to be bent;
    wherein the first bending portion is configured to perform the following bending actuation according to rotational operation input to the movable support portion, and
    wherein the movable support portion couples the connecting portion support portion and the movement portion support portion to each other such that the movement portion rotational end portion is configured to rotate in the rotational direction about the center of the rotation linked with rotation of the connecting portion rotational end portion in the rotational direction about the center of the rotation.

2. The medical system according to claim 1,
    wherein the insertion master portion is configured to be switched between a locking state where the insertion master portion is inoperable and a free state where the insertion master portion is operable,
    the treatment master portion is configured to be switched between a locking state where the treatment master portion is inoperable and a free state where the treatment master portion is operable, and
    the medical system includes a releasing switch portion configured to make only one of the insertion master portion and the treatment master portion selectively in the free state.

3. The medical system according to claim 1, further comprising:
    a first said treatment slave apparatus and a second said treatment slave apparatus;
    a first said treatment master portion and a second said treatment master portion configured to control the first treatment slave apparatus and the second treatment slave apparatus, respectively;
    a first said support arm connecting portion and a second said support arm connecting portion coupling the movable portion to the first treatment master portion and the second treatment master portion, respectively, and
    wherein the first support arm connecting portion and the second support arm connecting portion extend toward sides opposite to each other relative to an axial direction of the insertion master portion.

* * * * *